(12) United States Patent
Okamoto et al.

(10) Patent No.: US 9,458,186 B2
(45) Date of Patent: Oct. 4, 2016

(54) POLYSACCHARIDE DERIVATIVE, METHOD FOR PRODUCING THE SAME, AND SEPARATING AGENT

(75) Inventors: Yoshio Okamoto, Harbin (CN); Junqing Li, Harbin (CN); Xiande Shen, Harbin (CN); Jun Shen, Harbin (CN); Haitao Qu, Harbin (CN); Guangshun Wu, Harbin (CN)

(73) Assignee: DAICEL CORPORATION, Osaka-shi, Osaka (JP)

( * ) Notice: Subject to any disclaimer, the term of this patent is extended or adjusted under 35 U.S.C. 154(b) by 274 days.

(21) Appl. No.: 13/808,717

(22) PCT Filed: Jul. 5, 2011

(86) PCT No.: PCT/JP2011/065363
§ 371 (c)(1),
(2), (4) Date: Jan. 7, 2013

(87) PCT Pub. No.: WO2012/005245
PCT Pub. Date: Jan. 12, 2012

(65) Prior Publication Data
US 2013/0116418 A1    May 9, 2013

(30) Foreign Application Priority Data
Jul. 9, 2010  (CN) .......................... 2010 1 0228355

(51) Int. Cl.
| | | |
|---|---|---|
| *C07H 15/20* | (2006.01) | |
| *C07H 1/00* | (2006.01) | |
| *C08B 15/06* | (2006.01) | |
| *C08B 33/00* | (2006.01) | |
| *B01J 20/285* | (2006.01) | |
| *B01J 20/29* | (2006.01) | |
| *B01J 20/32* | (2006.01) | |
| *C08B 15/00* | (2006.01) | |
| *C08L 1/08* | (2006.01) | |
| *C08L 3/14* | (2006.01) | |
| *G01N 30/88* | (2006.01) | |

(52) U.S. Cl.
CPC ............ *C07H 15/20* (2013.01); *B01J 20/285* (2013.01); *B01J 20/29* (2013.01); *B01J 20/3204* (2013.01); *B01J 20/3274* (2013.01); *C08B 15/00* (2013.01); *C08B 15/06* (2013.01); *C08B 33/00* (2013.01); *C08L 1/08* (2013.01); *C08L 3/14* (2013.01); *B01J 2220/4825* (2013.01); *G01N 2030/8877* (2013.01)

(58) Field of Classification Search
None
See application file for complete search history.

(56) References Cited

U.S. PATENT DOCUMENTS

| | | |
|---|---|---|
| 5,075,009 A | 12/1991 | Namikoshi et al. |
| 5,491,223 A | 2/1996 | Okamoto |
| 6,533,936 B1 | 3/2003 | Ikeda |
| 2004/0262229 A1 | 12/2004 | Okamoto et al. |
| 2007/0227957 A1 | 10/2007 | Murakami et al. |
| 2009/0105440 A1 | 4/2009 | Okamoto et al. |
| 2009/0124798 A1 | 5/2009 | Okamoto et al. |
| 2009/0264639 A1 | 10/2009 | Okamoto et al. |

FOREIGN PATENT DOCUMENTS

| | | | |
|---|---|---|---|
| EP | 2060588 A1 * | 5/2009 | ............ C08B 33/06 |
| EP | 2 145 903 A1 | 1/2010 | |
| JP | 60-226829 A | 11/1985 | |
| JP | H06-093002 A | 4/1994 | |
| JP | H07-285889 A | 10/1995 | |
| JP | 2005-017268 A | 1/2005 | |
| JP | 2006-150214 A | 6/2006 | |
| WO | WO92/15616 A1 | 9/1992 | |
| WO | WO2007/129658 A1 | 11/2007 | |
| WO | WO2007/129659 A1 | 11/2007 | |
| WO | WO2008/029785 A1 | 3/2008 | |

OTHER PUBLICATIONS

"Raw." Dictionary.com Unabridged. Random House, Inc. Jan. 20, 2015. <Dictionary.com http://dictionary.reference.com/browse/raw>.*
EPO Search Report dated Oct. 25, 2013 (7 pages).
"Chiral Stationary Phases for HPLC: Cellulose Tris(3,5-dimethylphenylcarbamate) and Tris(3,5-dichlorophenylcarbamate) Chemically Bonded to Silica Gel", by Y. Okamoto et al, Journal of Liquid Chromatography, vol. 10(8&9), pp. 1613-1628, 1987.
"Polysaccharide derivatives as useful chiral stationary phases in high-performance liquid chromatography*", by X. Chen et al, Pure Appl. Chem., vol. 79, No. 9, pp. 1561-1573, 2007.
"Preparation and Chiral Recognition of Polysaccharide-Based Selectors", by T. Ikai et al, Springer Berlin Heidelberg, pp. 33-52, 2010.
Xi Controlled Chiral Recognition of Cellulose Triphenylcarbamate Derivatives Supported on Silica Gel; Y. Okamoto, M. Kawashima and K. Hatada, J. Chromatogr., 363, 173 (1986).

(Continued)

*Primary Examiner* — Layla Berry
*Assistant Examiner* — Bahar Craigo
(74) *Attorney, Agent, or Firm* — Flynn, Thiel, Boutell & Tanis, P.C.

(57) ABSTRACT

An object of the present invention is to provide a novel polysaccharide derivative used for a separating agent for optical isomers. The novel polysaccharide derivative contains a structure in which a hydrogen atom of a hydroxyl group or an amino group at the 2-position in a structural unit of the polysaccharide is substituted with a monovalent group represented by the following general formula (1), and a hydrogen atom of a hydroxyl group or an amino group at the 3-position in the structural unit is substituted with a monovalent group represented by the following general formula (2):

$$R^1-NH-CO- \quad (1)$$

$$R^2-NH-CO- \quad (2)$$

where $R^1$ and $R^2$ represent substituted or unsubstituted aryl groups which are different from each other.

1 Claim, 20 Drawing Sheets

(56) References Cited

OTHER PUBLICATIONS

Thermal Dissociation of Urethans in Amines, T. Mukaiyama et al., J.Am. Chem. Soc., Jan. 5, 1957, 79(1), pp. 73-76.
The Thermal Dissociation of Aryl Carbanilates in Glyme, A.B. Lateff et al., J. Org. Chem., vol. 36, No. 16, 1971, pp. 2295-2298.
Notice of Reasons for Rejection of Japanese Patent Office issued in Application No. 2012-523876 with English Translation date of mailing Jul. 17, 2015 (8 pages).
Yuriko Kaida and Yoshio Okamoto, *Optical Resolution on Regioselectively Carbamoylated Cellulose and Amylose with 3,5-Dimethylphenyl and 3,5-Dichlorophenyl Isocyanates*, Bull. Chem. Soc. Jpn., 1993, vol. 66, No. 8, pp. 2225-2232.
Takateru Kubota, Chiyo Yamamoto, Yoshio Okamoto, *Preparation and Chiral Recognition Ability of Cellulose 3,5-Dimethylphenylcarbamate Immobilized on Silica Gel through Radical Polymerization*, Journal of Polymer Science Part A Polymer Chemistry, 2003, vol. 41, pp. 3703-3712.
Takateru Kubota, Chiyo Yamamoto, Yoshio Okamoto, *Phenylcarbamate Derivatives of Cellulose and Amylose Immobilized onto Silica Gel as Chiral Stationary Phases for High-Performance Liquid Chromatography*, Journal of Polymer Science Part A Polymer Chemistry, 2004, vol. 42, pp. 4704-4710.
Bezhan Chankvetadze et al., *High-performance liquid chromatographic enantioseparations on capillary columns containing cross-linked polysaccharide phenylcarbamate derivatives attached to monolithic silica*, Journal of Separation Science, 2006, vol. 29(13), pp. 1988-1995.

* cited by examiner

POLYSACCHARIDE DERIVATIVE, METHOD FOR PRODUCING THE SAME, AND SEPARATING AGENT

TECHNICAL FIELD

The present invention relates to a novel polysaccharide derivative, a method for producing the polysaccharide derivative, and a separating agent containing the polysaccharide derivative.

BACKGROUND ART

A polysaccharide derivative obtained by modifying the hydroxyl groups or amino groups of a polysaccharide with various types of substituents is known to serve as a chiral stationary phase in chromatography to show a high optical resolution, and a large number of kinds of polysaccharide derivatives have been heretofore synthesized.

As such a polysaccharide derivative useful as a separating agent for optical isomers, for example, a polysaccharide derivative that contains a structure in which hydroxyl groups or amino groups at 2-position and 3-position (and 6-position) of the polysaccharide are substituted with different specific substituents is proposed (see Patent Document 1). As another polysaccharide derivative useful as a separating agent for optical isomers, a polysaccharide derivative is proposed in which hydroxyl groups or amino groups of the polysaccharide are substituted with two or more different specific kinds of substituents, and particularly a substituent at the 2-position and 3-position and a substituent at the 6-position are different from each other (see Patent Document 2).

CITED LIST

Patent Documents

Patent Document 1: WO 2008/029785
Patent Document 2: WO 1992/015616

SUMMARY OF INVENTION

Technical Problem

However, there is room for further studies on polysaccharide derivatives having a specific kind of a substituent at a specific position, particularly on polysaccharide derivatives having specific substituents different from each other at the 2-position and the 3-position that are difficult to distinguish in the introduction of the substituents into a hexose.

The present invention has been achieved in consideration of the above-mentioned situation, and an object of the present invention is to provide a novel polysaccharide derivative capable of being used for a separating agent for optical isomers, a method for producing the polysaccharide derivative, and a separating agent containing the polysaccharide derivative.

Solution to Problem

In order to achieve the above-mentioned object, the present invention provides a polysaccharide derivative containing a structure in which a hydrogen atom of a hydroxyl group or an amino group at the 2-position in a structural unit of the polysaccharide is substituted with a monovalent group represented by the following general formula (1), and a hydrogen atom of a hydroxyl group or an amino group at the 3-position in the structural unit is substituted with a monovalent group represented by the following general formula (2):

$$R^1\text{—NH—CO—} \tag{1}$$

$$R^2\text{—NH—CO—} \tag{2}$$

in which $R^1$ and $R^2$ represent substituted or unsubstituted aryl groups which are different from each other.

The present invention further provides a polysaccharide derivative in which the above-mentioned polysaccharide is cellulose or amylose. The present invention still further provides a polysaccharide derivative in which the $R^1$ is a 3,5-dichlorophenyl group, and the $R^2$ is a 3,5-dimethylphenyl group.

The present invention provides a method for producing a polysaccharide derivative, including the step of causing a polysaccharide derivative raw material containing a structure in which the hydrogen atoms of the hydroxyl or amino groups at the 2-position and the 3-position in a structural unit of the polysaccharide are substituted with monovalent groups identical to each other represented by the following general formula (1):

$$R^1\text{—NH—CO—} \tag{1},$$

in which $R^1$ represents a substituted or unsubstituted aryl group, to react with a compound represented by the following general formula (3):

$$R^2\text{—NCO} \tag{3},$$

in which $R^2$ represents a substituted or unsubstituted aryl group different from $R^1$, to thereby substitute one of the monovalent groups represented by the above general formula (1) with which the hydrogen atoms of the hydroxyl or amino groups at the 2-position and the 3-position have been substituted, with a monovalent group represented by the following general formula (2):

$$R^2\text{—NH—CO—} \tag{2},$$

in which $R^2$ has the same definition as the $R^2$ in the above general formula (3).

The present invention further provides a separating agent containing the above-mentioned polysaccharide derivative.

Advantageous Effects of Invention

The present invention can provide a novel polysaccharide derivative capable of being used for a separating agent for optical isomers, a method for producing the polysaccharide derivative, and a separating agent containing the polysaccharide derivative.

DESCRIPTION OF EMBODIMENTS

Figure 1:
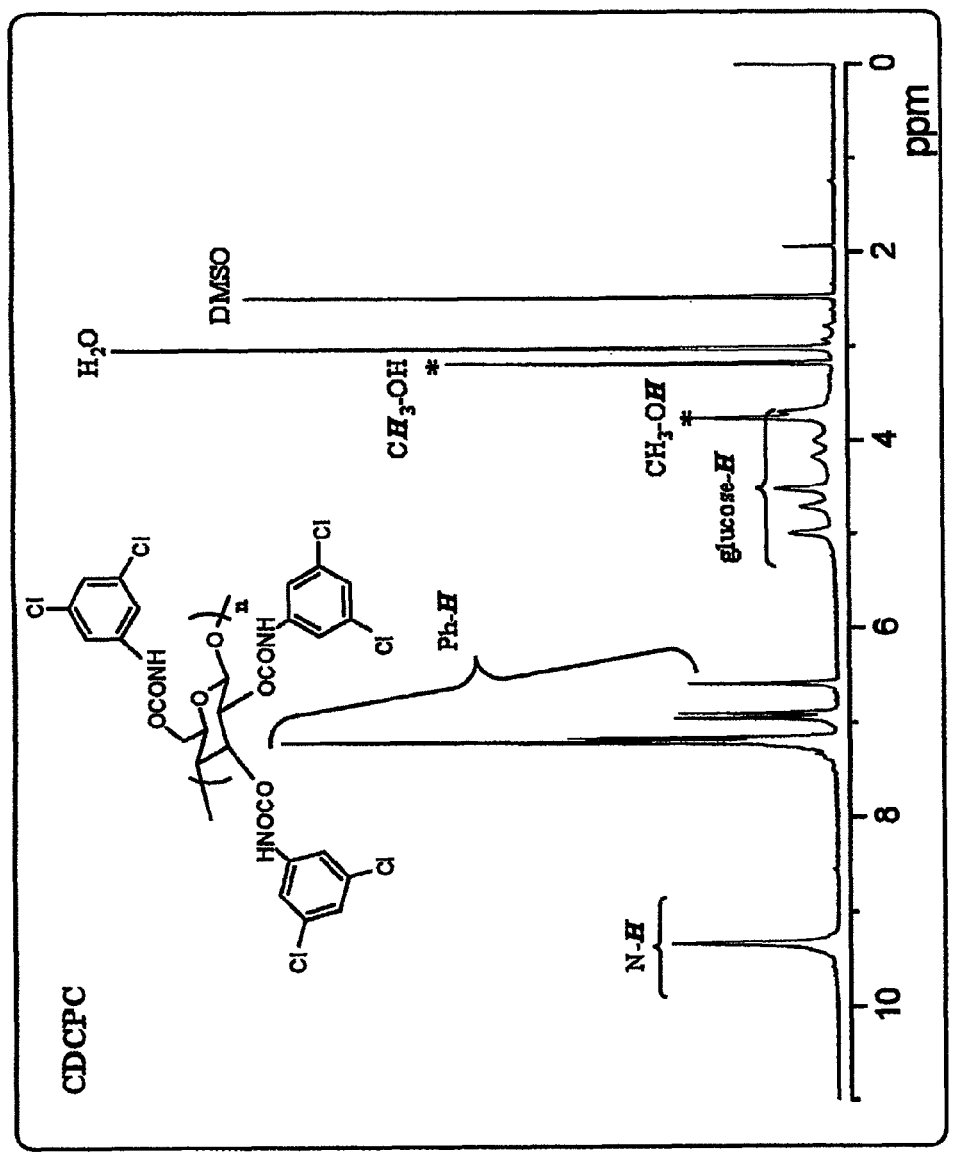
FIG. 1 is a view showing a $^1$H-NMR spectrum of cellulose tris(3,5-dichlorophenylcarbamate).
Figure 2:
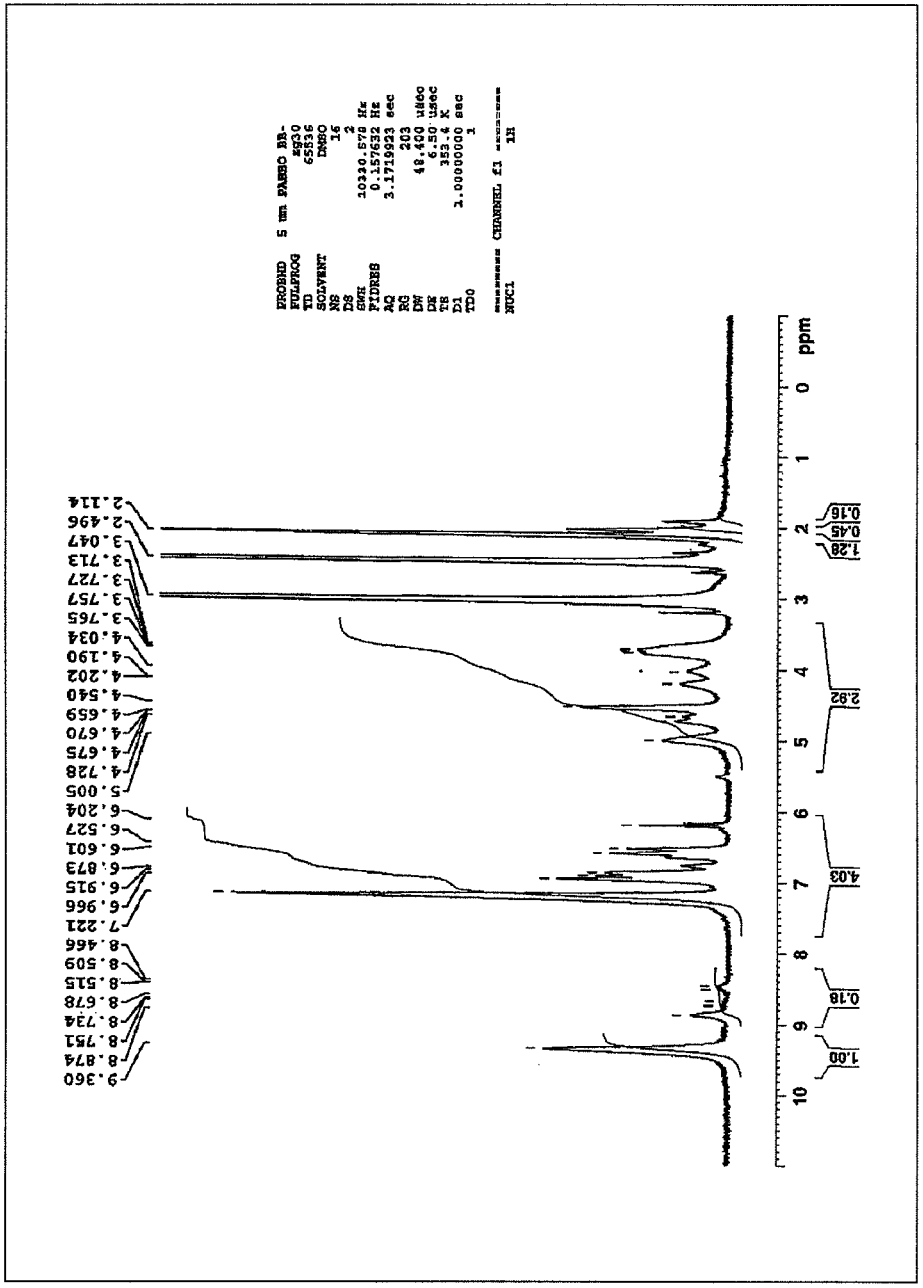
FIG. 2 is a view showing a $^1$H-NMR spectrum of a reaction product when the polysaccharide derivative according to the present invention is produced.
Figure 3:
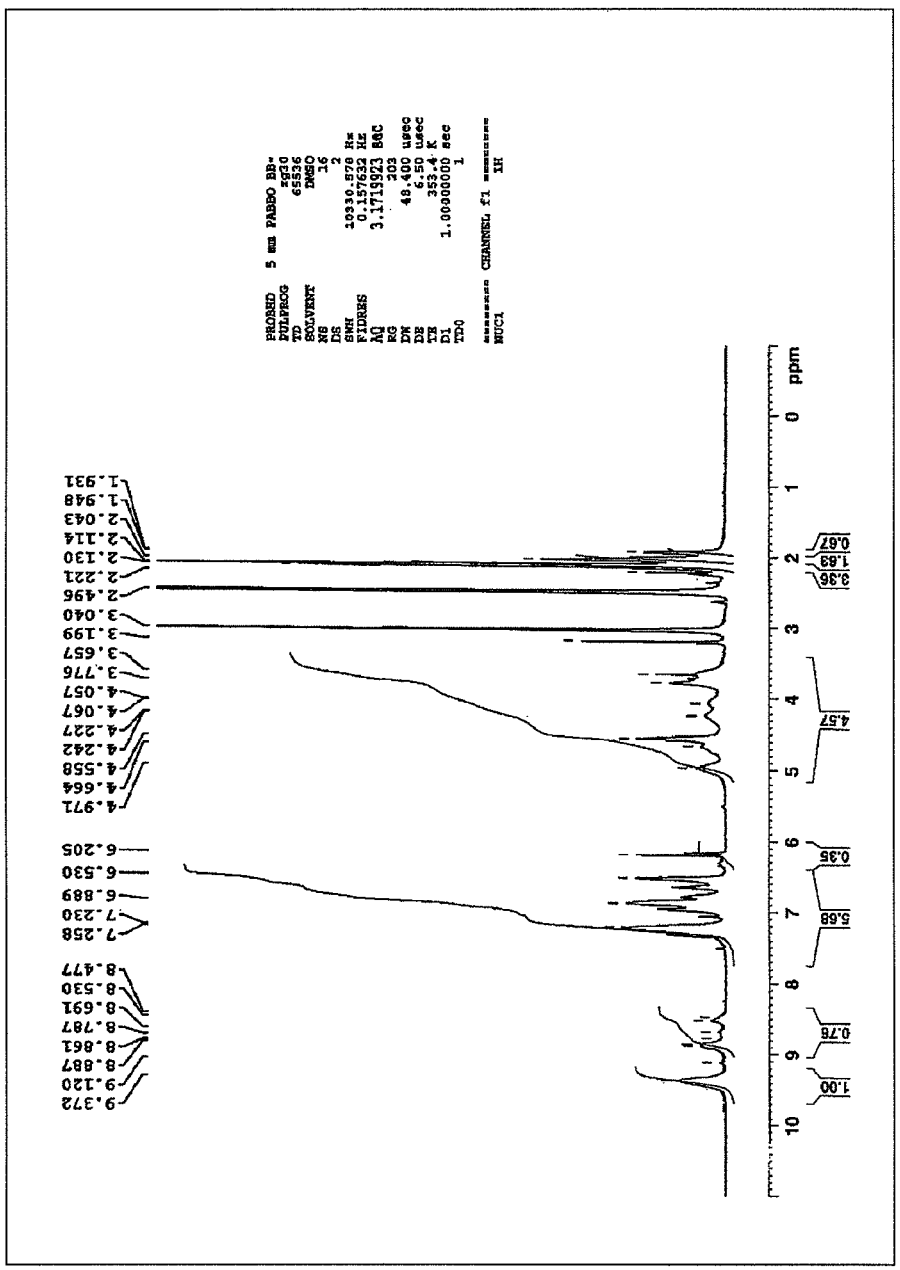
FIG. 3 is a view showing a $^1$H-NMR spectrum of a reaction product when the polysaccharide derivative according to the present invention is produced.
Figure 4:
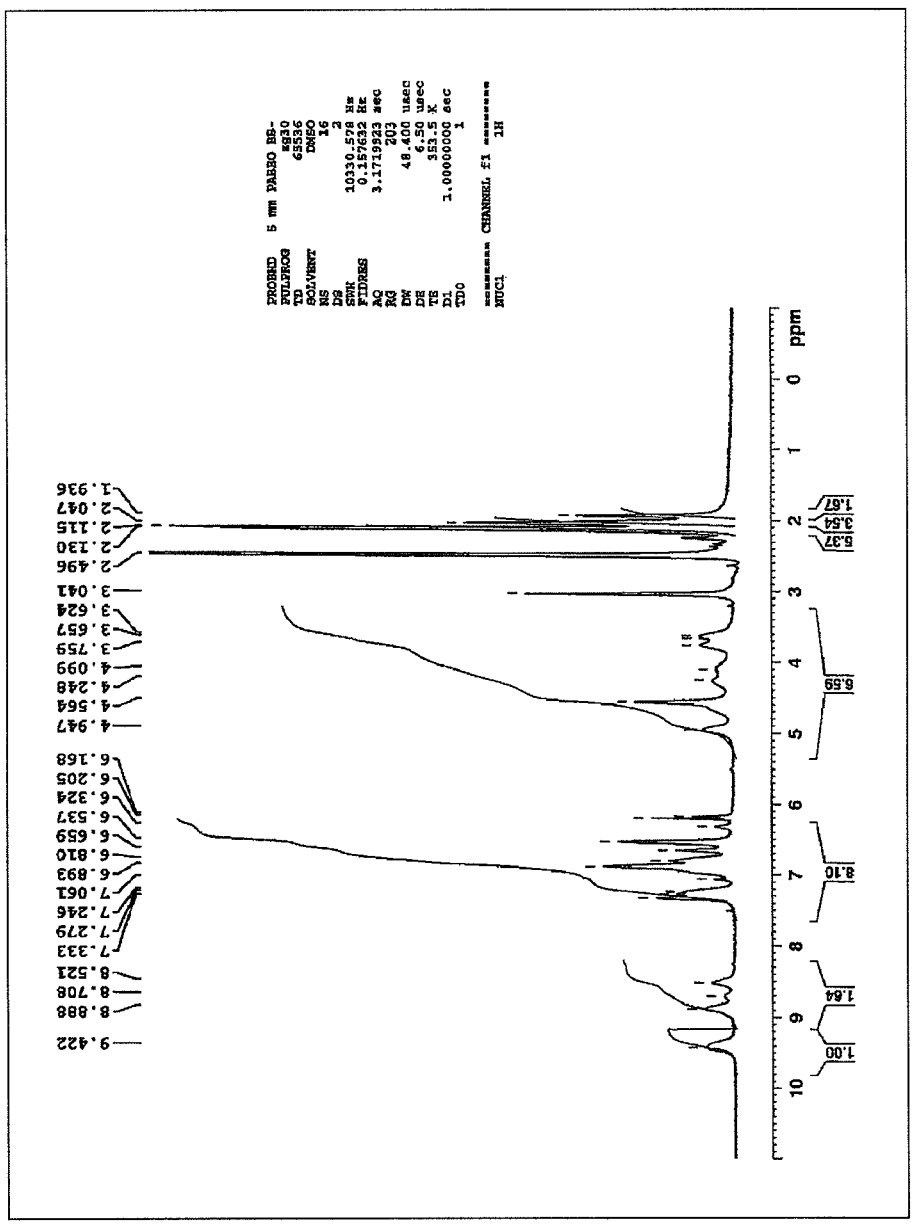
FIG. 4 is a view showing a $^1$H-NMR spectrum of a reaction product when the polysaccharide derivative according to the present invention is produced.
Figure 5:
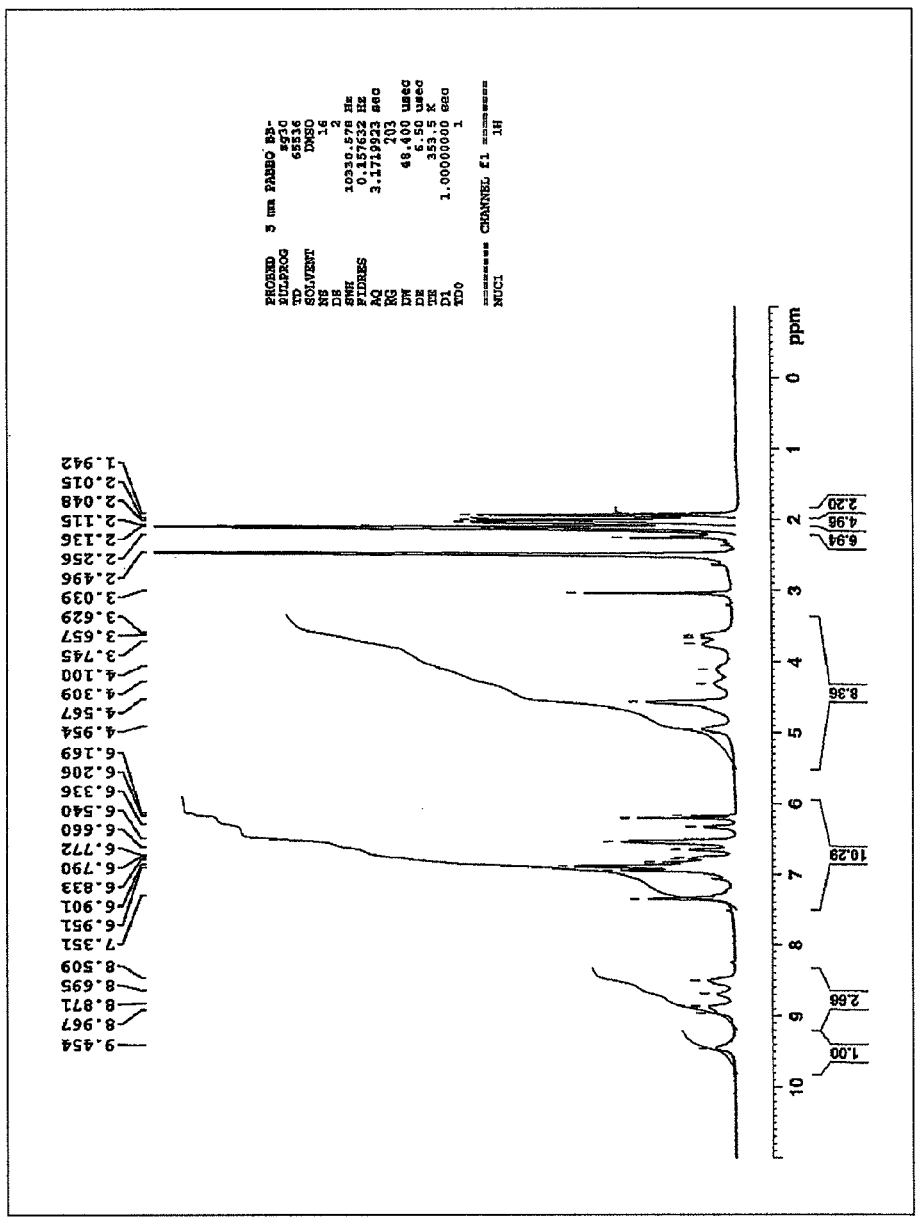
FIG. 5 is a view showing a $^1$H-NMR spectrum of a reaction product when the polysaccharide derivative according to the present invention is produced.
Figure 6:
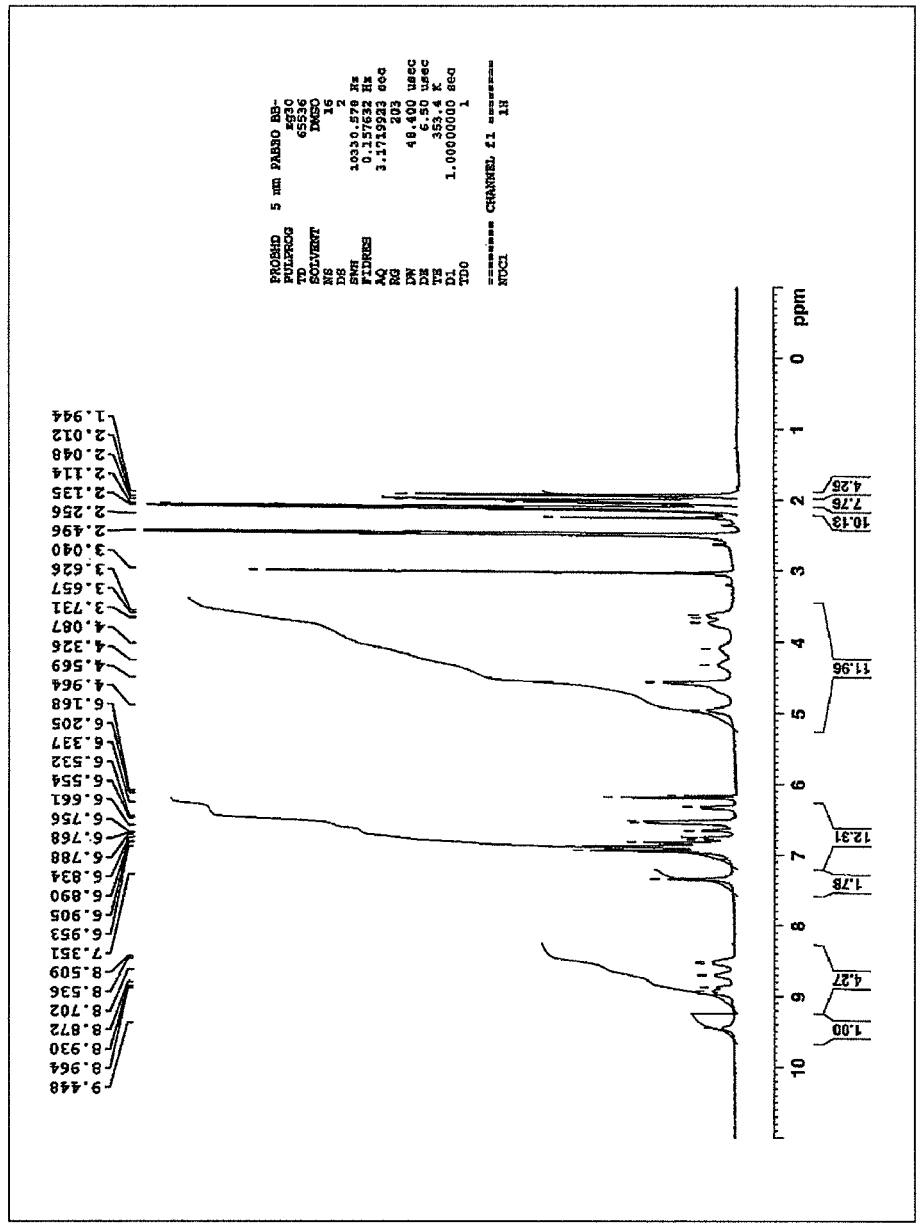
FIG. 6 is a view showing a $^1$H-NMR spectrum of a reaction product when the polysaccharide derivative according to the present invention is produced.
Figure 7:
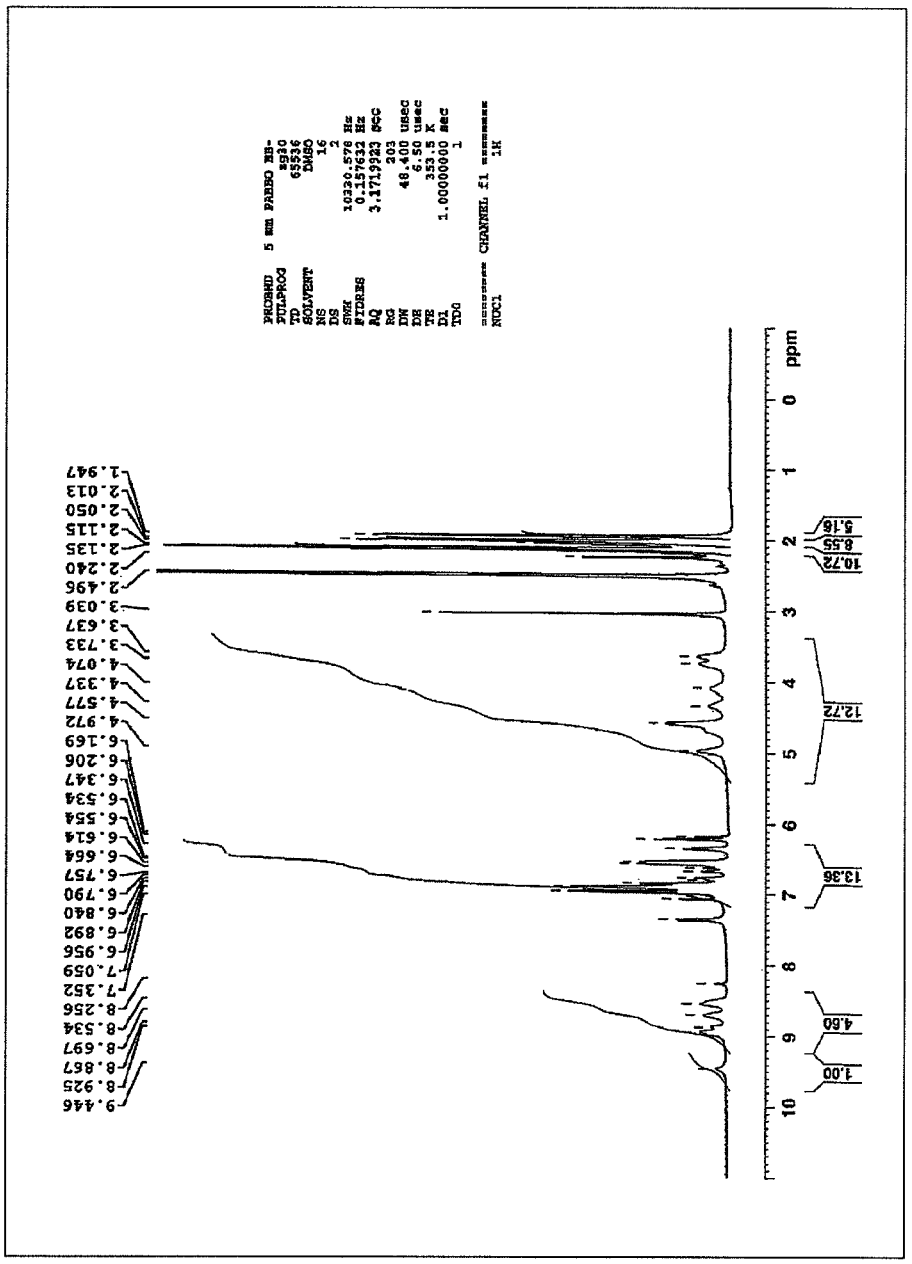
FIG. 7 is a view showing a $^1$H-NMR spectrum of a reaction product when the polysaccharide derivative according to the present invention is produced.
Figure 8:
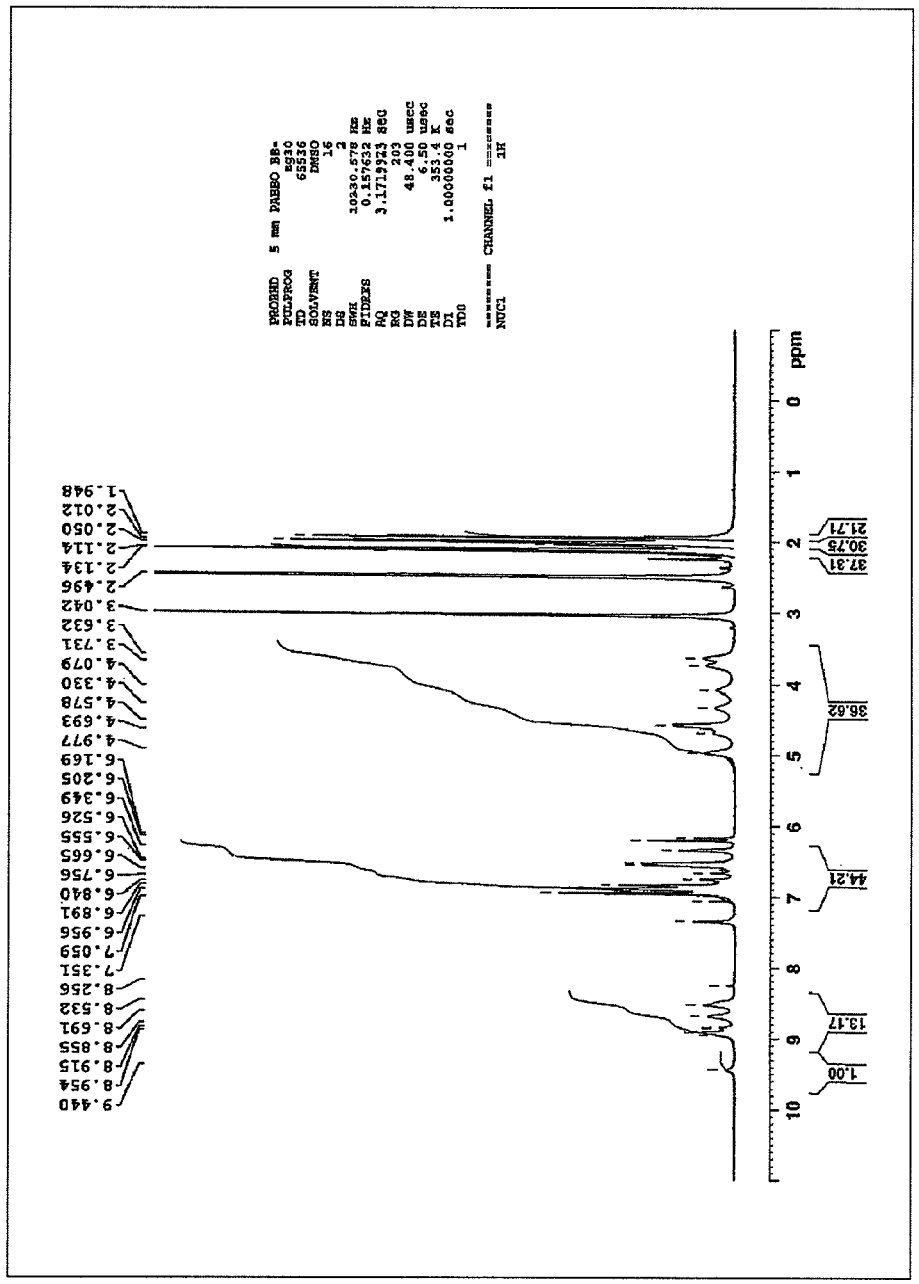
FIG. 8 is a view showing a $^1$H-NMR spectrum of a reaction product when the polysaccharide derivative according to the present invention is produced.
Figure 9:
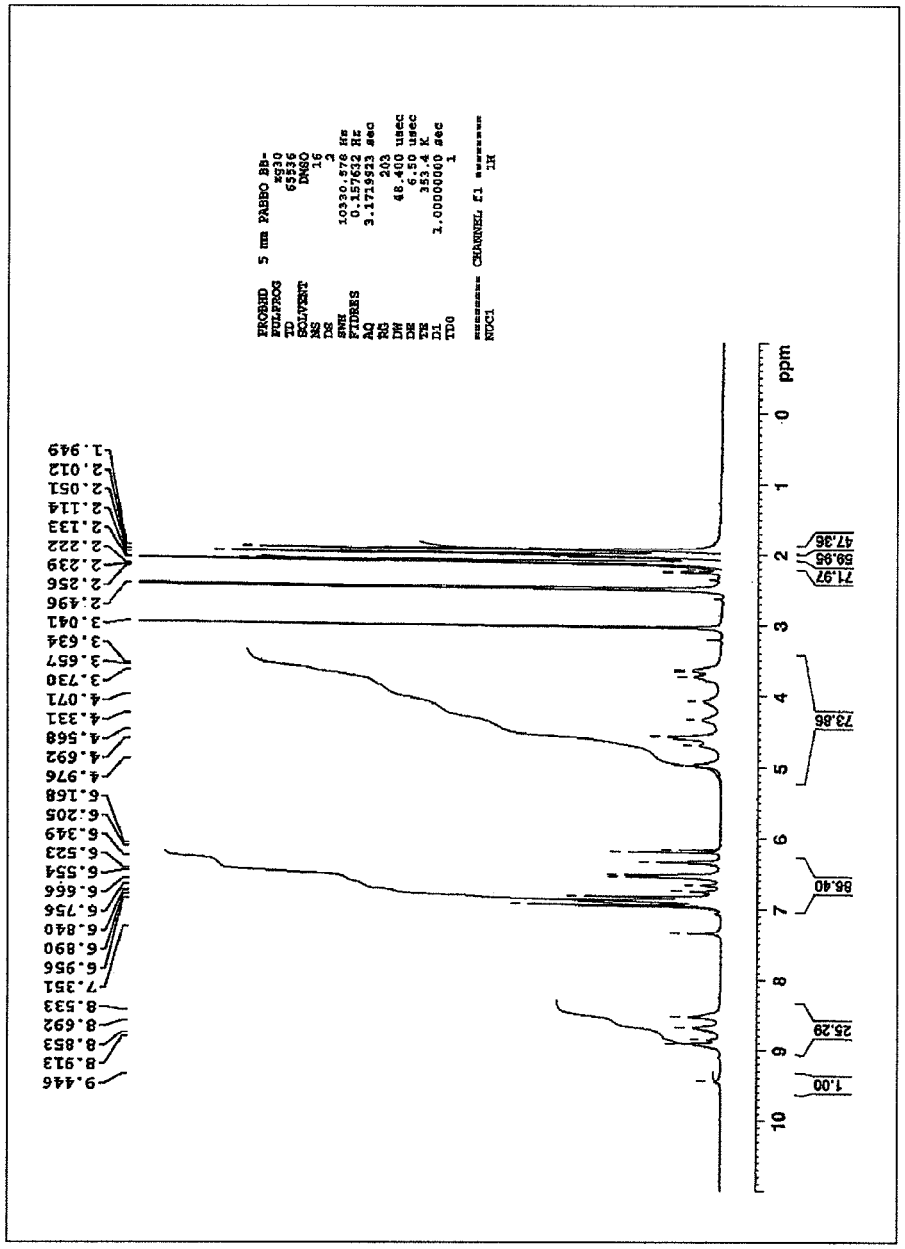
FIG. 9 is a view showing a $^1$H-NMR spectrum of a reaction product when the polysaccharide derivative according to the present invention is produced.

Hereinafter, an embodiment (hereinafter, referred to simply as "the present embodiment") in order to carry out the present invention will be described in detail, as required, with reference to the drawings. However, the present invention is not limited to the following present embodiment, and various changes and modifications may be made without departing from the gist.

The polysaccharide derivative according to the present embodiment contains a structure (hereinafter, referred to as "a predetermined structure") in which a hydrogen atom of a hydroxyl group or an amino group at the 2-position in a structural unit of the polysaccharide is substituted with a monovalent group represented by the following general formula (1), and a hydrogen atom of a hydroxyl group or an amino group at the 3-position in the structural unit is substituted with a monovalent group represented by the following general formula (2). The polysaccharide derivative may be constituted only of the predetermined structure, and may further contain another structure.

$R^1$—NH—CO— (1)

$R^2$—NH—CO— (2)

where $R^1$ and $R^2$ each represent substituted or unsubstituted aryl groups which are different from each other. In the present specification, "hydrogen atom of an amino group" means one hydrogen atom out of two hydrogen atoms.

The above-mentioned polysaccharide is not particularly limited as long as at least having hydroxyl groups or amino groups at the 2-position and the 3-position. Examples of such a polysaccharide include β-1,4-glucan (cellulose), α-1,4-glucan (amylose, amylopectin), α-1,6-glucan (dextran), β-1,6-glucan (pustulan), β-1,3-glucan (curdlan, sizofiran), α-1,3-glucan, β-1,2-glucan (Crown Gall polysaccharide), β-1,4-galactan, β-1,4-mannan, α-1,6-mannan, β-1,2-fructan (inulin), β-2,6-fructan (levan), β-1,4-xylan, β-1,3-xylan, β-1,4-chitosan, β-1,4-N-acetylchitosan (chitin), pullulan, agarose, alginic acid, α-cyclodextrin, β-cyclodextrin, γ-cyclodextrin, nigeran, and starch containing amylose.

Among these, preferable polysaccharides are cellulose and amylose, and a more preferable one is cellulose, from the viewpoint of the optical resolving power.

The number-average polymerization degree (an average number of pyranose or furanose rings contained in one molecule) of a polysaccharide is preferably 5 or higher, more preferably 10 or higher; and there is particularly no upper limit, but the number-average polymerization degree is preferably 1,000 or lower from the viewpoint of the easiness of handling, more preferably 5 to 1,000, still more preferably 10 to 1,000, and particularly preferably 10 to 500.

In the above general formulae (1) and (2), $R^1$ and $R^2$ each represent substituted or unsubstituted aryl groups which are different from each other. The aryl group includes aryl groups containing a condensed ring having 6 to 30 carbon atoms, and examples include a phenyl group, an indenyl group, a naphthyl group, an anthryl group, a phenanthryl group, a fluorenyl group, a pyrenyl group, a biphenyl group, and a terphenyl group. Among these, a phenyl group is preferable from the viewpoint of the optical resolving power.

Examples of a substituent that $R^1$ and $R^2$ may have include one or more substituents selected from the group consisting of: hydrocarbon groups that have 1 to 12 carbon atoms and may contain a hetero atom; a cyano group; halogen atoms; a hydroxy group; a nitro group; an amino group; and di(alkyl having 1 to 8 carbon atoms)amino groups (that is, amino groups having alkyl groups having 1 to 8 carbon atoms as substituents). Among these, hydrocarbon groups that have 1 to 12 carbon atoms and may contain a hetero atom, and halogen atoms are preferable. Preferable hydrocarbon groups that have 1 to 12 carbon atoms and may contain a hetero atom are alkyl groups having 1 or 2 carbon atoms, and a preferable halogen atom is a chlorine atom.

Monovalent groups represented by the above general formulae (1) and (2) (hereinafter, substituted carbamoyl groups in which one substituted or unsubstituted aryl group is bonded to a carbamoyl nitrogen atom like the ones represented by the above general formulae (1) and (2) are collectively referred to as a "predetermined carbamoyl group") may not be substituted for all of the hydrogen atoms of a hydroxyl group or an amino group at the corresponding positions in the above-mentioned structural unit as long as the substitution is in the range of being capable of providing an effect of the optical resolving power by these groups. The degree of substitution of a predetermined carbamoyl group to the polysaccharide derivative according to the present embodiment is preferably 70 to 100%, more preferably 80 to 100%, and particularly preferably 100%.

Here, the degree of substitution (%) is defined as follows. That is, in the polysaccharide derivative according to the present embodiment, the degree of substitution (%) is a ratio of the total number of a predetermined carbamoyl group in the polysaccharide derivative according to the present embodiment to the total number of hydroxyl groups or amino groups in the above-mentioned structural units in the case where the predetermined carbamoyl group is assumed to be substituted for all of the hydrogen atoms of the hydroxyl groups or hydrogen atoms of the amino groups in the structural units. The degree of substitution can be determined by utilizing a known analysis method including NMR and an elemental analysis capable of identifying one or both of the kind and the bonding position of a predetermined carbamoyl group, and can also be determined depending on the kind of a predetermined carbamoyl group or the bonding position of a substituent.

For example, in the case where a predetermined carbamoyl group is substituted only for hydrogen atoms of hydroxyl groups in the polysaccharide derivative according to the present embodiment, the above-mentioned degree of substitution is a numerical value obtained by multiplying a ratio of the number of the predetermined carbamoyl groups after the substitution to the total number of the hydroxyl groups of the polysaccharide by 100. In the case where a predetermined carbamoyl group is substituted only for the hydrogen atoms of the amino groups, the degree of substitution is a numerical value obtained by multiplying a ratio of the number of the predetermined carbamoyl group after the substitution to the total number of the amino groups of the polysaccharide by 100. Further in the case where a predetermined carbamoyl group is substituted for hydrogen atoms of hydroxyl groups and amino groups, the degree of substitution is a numerical value obtained by multiplying a ratio of a total number of the predetermined carbamoyl groups after the substitution to the total of a total number of the hydroxyl groups and a total number of the amino groups of the polysaccharide by 100.

The 2-position substituent obtained by substituting a hydrogen atom of a hydroxyl group or an amino group with a monovalent group represented by the above general formula (1) (hereinafter, referred to as a "predetermined 2-position substituent") is preferably a substituent obtained by substituting a hydrogen atom of a hydroxyl group with a monovalent group represented by the above general formula (1). In the predetermined 2-position substituent, $R^1$ is preferably a substituted or unsubstituted phenyl group, more preferably a phenyl group having substituents at the 3-position and the 5-position, still more preferably a 3,5-dichlorophenyl group or a 3,5-dimethylphenyl group, and particularly preferably a 3,5-dichlorophenyl group.

The 3-position substituent obtained by substituting a hydrogen atom of a hydroxyl group or an amino group with a monovalent group represented by the above general formula (2) (hereinafter, referred to as a "predetermined 3-position substituent") is different from the predetermined 2-position substituent. The predetermined 3-position substituent is preferably a substituent obtained by substituting a hydrogen atom of a hydroxyl group with a monovalent group represented by the above general formula (2). In the predetermined 3-position substituent, $R^2$ is preferably a substituted or unsubstituted phenyl group, more preferably a phenyl group having substituents at the 3-position and the 5-position, still more preferably a 3,5-dichlorophenyl group or a 3,5-dimethylphenyl group, and particularly preferably a 3,5-dimethylphenyl group.

The polysaccharide derivative according to the present embodiment, in the case where the structural unit is a hexose, may contain a structure in which the 6-position carbon atom further has a substituent. The 6-position substituent in the structural unit is preferably a substituent obtained by substituting a hydrogen atom of a hydroxyl group or an amino group at the 6-position with a predetermined carbamoyl group, and more preferably a substituent obtained by substituting a hydrogen atom of a hydroxyl group at the 6-position with a predetermined carbamoyl group. The 6-position substituent is preferably the same substituent as the predetermined 2-position substituent or the predetermined 3-position substituent, and more preferably the same substituent as the predetermined 3-position substituent.

The polysaccharide derivative according to the present embodiment, as well as containing the above-mentioned predetermined structure, may contain a structure, as a structure other than the predetermined structure, having substituents excluding the above-mentioned predetermined 2-position substituent and predetermined 3-position substituent as at least one of a 2-position substituent and a 3-position substituent. The polysaccharide derivative according to the present embodiment may contain a structure, as a structure other than the predetermined structure, having a 2-position substituent and a 3-position substituent different from each other. In the structure, one of the 2-position substituent and the 3-position substituent different from each other is preferably a substituent obtained by substituting a hydrogen atom of a hydroxyl group or an amino group with a predetermined carbamoyl group, and more preferably a substituent obtained by substituting a hydrogen atom of a hydroxyl group with a predetermined carbamoyl group.

The polysaccharide derivative according to the present embodiment may contain a structure, as a structure other than the predetermined structure, in which a 2-position substituent and a 3-position substituent are identical to each other. The 2-position substituent and 3-position substituent that are identical to each other are preferably a substituent obtained by substituting a hydrogen atom of a hydroxyl group or an amino group with a predetermined carbamoyl group, and more preferably a substituent obtained by substituting a hydrogen atom of a hydroxyl group with a predetermined carbamoyl group. The above 2-position substituent and 3-position substituent that are identical to each other are preferably the same as one of the 2-position and 3-position substituents in the above predetermined structure.

In the polysaccharide derivative according to the present embodiment, in the case where the hydrogen atoms of the hydroxyl or amino groups at the 2-position and the 3-position in the structural unit of the polysaccharide are substituted only with predetermined carbamoyl groups, and in the case where the predetermined carbamoyl groups are composed of two kinds of carbamoyl groups, the molar ratio (a:b, hereinafter, the same) of both the carbamoyl groups at the 2-position is preferably 80:20 to 30:70, and more preferably 50:50 to 40:60. The ratio of both the carbamoyl groups at the 3-position in this case is preferably 40:60 to 10:90, and more preferably 15:85 to 10:90. The two kinds of carbamoyl groups are both preferably substituted or unsubstituted phenyl groups as the substituted or unsubstituted aryl groups, more preferably phenyl groups having substituents at the 3-position and the 5-position, and still more preferably a 3,5-dichlorophenyl group or a 3,5-dimethylphenyl group. It is particularly preferable that among the two kinds of carbamoyl groups, one carbamoyl group having a ratio represented by the above "a" has a 3,5-dichlorophenyl group as the substituted or unsubstituted aryl group, and one carbamoyl group having a ratio represented by the above "b" has a 3,5-dimethylphenyl group.

In the polysaccharide derivative according to the present embodiment, in the case where hydrogen atoms of a hydroxyl group or an amino group at the 2-position, the 3-position and the 6-position in the structural unit of the polysaccharide are substituted only with predetermined carbamoyl groups, and in the case where the predetermined carbamoyl groups are composed of two kinds of carbamoyl groups, the molar ratio (a:b, hereinafter, the same) of both the carbamoyl groups at the 2-position is preferably 80:20 to 30:70, and more preferably 50:50 to 40:60. The ratio of both the carbamoyl groups at the 3-position in this case is preferably 40:60 to 10:90, and more preferably 15:85 to 10:90. The ratio of both the carbamoyl groups further at the 6-position in this case is preferably 0:100. The two kinds of carbamoyl groups are both preferably substituted or unsubstituted phenyl groups as the substituted or unsubstituted aryl groups, more preferably phenyl groups having substituents at the 3-position and the 5-position, and still more preferably a 3,5-dichlorophenyl group or a 3,5-dimethylphenyl group. It is particularly preferable that among the two kinds of carbamoyl groups, one carbamoyl group having a ratio represented by the above "a" has a 3,5-dichlorophenyl group as the substituted or unsubstituted aryl group, and one carbamoyl group having a ratio represented by the above "b" has a 3,5-dimethylphenyl group.

The polysaccharide derivative according to the present embodiment can be produced by the following method. That is, the production method of the polysaccharide derivative according to the present embodiment includes a step of causing a polysaccharide derivative (hereinafter, referred to as a "raw material polysaccharide derivative") being a raw material containing a structure in which hydrogen atoms of hydroxyl groups or amino groups at the 2-position and the 3-position in a structural unit of the polysaccharide are substituted with monovalent groups identical to each other represented by the above general formula (1) to react with a compound represented by the following general formula (3):

$$R^2\text{—NCO} \qquad (3)$$

to thereby substitute one of the monovalent groups represented by the above general formula (1) with which hydrogen atoms of hydroxyl groups or amino groups at the 2-position and the 3-position have been substituted, with a monovalent group represented by the above general formula (2). In the formula (3), $R^2$ has the same definition as the $R^2$ in the general formula (2).

In the production method according to the present embodiment, more specifically, a polysaccharide derivative as a raw material is first prepared. The polysaccharide derivative as a raw material may be synthesized by a known method using a polysaccharide already described in detail as a raw material, or may be a commercially available product. The polysaccharide derivative as a raw material is preferably cellulose derivatives and amylose derivatives, and more preferably cellulose derivatives, from the viewpoint of speedily and securely obtaining a target polysaccharide derivative.

Examples of the polysaccharide derivative as a raw material include cellulose tris(3,5-dichlorophenylcarbamate), cellulose tris(3,5-dimethylphenylcarbamate), cellulose tris-phenylcarbamate, cellulose tris(4-methylphenylcarbamate) and cellulose tris(4-chlorophenylcarbamate). Among these, cellulose tris(3,5-dichlorophenylcarbamate) and cellulose tris(3,5-dimethylphenylcarbamate) are preferable, and from the viewpoint of speedily obtaining a target polysaccharide derivative, cellulose tris(3,5-dichlorophenylcarbamate) is more preferable.

Then, the polysaccharide derivative as a raw material is caused to react with a compound represented by the above general formula (3) (hereinafter, referred to as a "predetermined isocyanate"). Thereby, the polysaccharide derivative according to the present embodiment can be synthesized by substituting one of the monovalent groups represented by the above general formula (1) with which the hydrogen atoms of the hydroxyl or amino groups at the 2-position and the 3-position have been substituted, with a monovalent group represented by the above general formula (2). Since this reaction is an equilibrium reaction between a carbamate and an isocyanate, the amount of the monovalent group represented by the above general formula (2) to be substituted can be controlled by regulating the amount of a predetermined isocyanate to be used, a solvent, the reaction temperature and the reaction time.

For example, a case where a cellulose tris(3,5-dichlorophenylcarbamate) as the polysaccharide derivative as a raw material and 3,5-dimethylphenyl isocyanate as the predetermined isocyanate are used will be described. The cellulose tris(3,5-dichlorophenylcarbamate) is dissolved in a mixed solvent of DMA/pyridine/LiCl; and an excessive amount of 3,5-dimethylphenyl isocyanate with respect to a 3,5-dichlorophenylcarbamoyl group in the cellulose tris(3,5-dichlorophenylcarbamate) is added to the mixture, and is caused to react, for example, at 80° C. Thereby, the 3,5-dichlorophenylcarbamoyl group is substituted with a 3,5-dimethylphenylcarbamoyl group. At this time, along with lapse of time, the substitution of the 3,5-dichlorophenylcarbamoyl group is initiated at the 6-position, and the substitution of the 3,5-dichlorophenylcarbamoyl group is then initiated at the 3-position and the 2-position in this order. As a result, a polysaccharide derivative is obtained which contains a structure in which a hydrogen atom of the hydroxyl group at the 2-position in the structural unit of the cellulose is substituted with a 3,5-dichlorophenylcarbamoyl group, and a hydrogen atom of the hydroxyl group at the 3-position is substituted with a 3,5-dimethylphenylcarbamoyl group, and/or a structure in which a hydrogen atom of the hydroxyl group at the 2-position in the structural unit of the cellulose is substituted with a 3,5-dimethylphenylcarbamoyl group, and a hydrogen atom of the hydroxyl group at the 3-position is substituted with a 3,5-dichlorophenylcarbamoyl group.

Further for example, a case where a cellulose tris(3,5-dimethylphenylcarbamate) as the polysaccharide derivative as a raw material and 3,5-dichlorophenyl isocyanate as the predetermined isocyanate are used will be described. The cellulose tris(3,5-dimethylphenylcarbamate) is dissolved in a mixed solvent of DMA/pyridine/LiCl; and an excessive amount of 3,5-dichlorophenyl isocyanate with respect to a 3,5-dimethylphenylcarbamoyl group in the cellulose tris(3,5-dimethylphenylcarbamate) is added to the mixture, and is caused to react, for example, at 80° C. Thereby, the 3,5-dimethylphenylcarbamoyl group is substituted with a 3,5-dichlorophenylcarbamoyl group. At this time, along with a lapse of time, the substitution of the 3,5-dimethylphenylcarbamoyl group is initiated at the 6-position, and the substitution of the 3,5-dimethylphenylcarbamoyl group is then initiated at the 3-position and the 2-position in this order. As a result, a polysaccharide derivative is obtained which contains a structure in which a hydrogen atom of the hydroxyl group at the 2-position in the structural unit of the cellulose is substituted with a 3,5-dimethylphenylcarbamoyl group, and a hydrogen atom of the hydroxyl group at the 3-position is substituted with a 3,5-dichlorophenylcarbamoyl group, and/or a structure in which a hydrogen atom of the hydroxyl group at the 2-position in the structural unit of the cellulose is substituted with a 3,5-dichlorophenylcarbamoyl group, and a hydrogen atom of the hydroxyl group at the 3-position is substituted with a 3,5-dimethylphenylcarbamoyl group.

A solvent used in the above reaction is not particularly limited as long as it is a solvent which dissolves the polysaccharide derivative as a raw material, and examples include amide-based solvents such as DMAc and DMF, pyridine-based solvents such as pyridine and quinoline, dimethyl sulfoxide, and mixed solvents thereof. The solvent may contain an ionic compound promoting the dissolution of the polysaccharide derivative as a raw material. Examples of such an ionic compound include lithium halides such as LiCl and LiBr. The reaction temperature and the reaction time may be regulated as desired.

The polysaccharide derivative according to the present embodiment can be used by being contained in a separating agent, and can be used particularly for a separating agent for optical isomers. The separating agent for optical isomers may be constituted only of the polysaccharide derivative according to the present embodiment, of a carrier such as silica gel and the polysaccharide derivative according to the present embodiment carried on the carrier, of an integral type to be integrally stored in a column, or in the form of particles to be packed in a column.

The separating agent for optical isomers is produced as in the case of known separating agents for optical isomers containing polysaccharide derivatives, except for using the polysaccharide derivative according to the present embodiment. More specifically, a separating agent for optical isomers can be produced by making the polysaccharide derivative according to the present embodiment carried on a carrier, or pulverizing the polysaccharide derivative itself or forming it into spherical particles by a known method (for example, a method described in Japanese Patent Application Laid-Open No. 7-285889). "Carrying" used here refers to a state where the polysaccharide derivative is immobilized on the carrier. As a carrying method, known carrying methods can be applied; and methods can be applied such as the physical adsorption between the polysaccharide derivative and the carrier, the chemical bond between the polysaccharide derivative and the carrier, the chemical bond between polysaccharide derivatives, the chemical bond between one of or both of the polysaccharide derivative and the carrier and the third component, the light irradiation to the polysaccharide derivative, and a radical reaction (see, for example, Japanese Patent Application Laid-Open No. 6-93002).

Examples of the carrier include porous organic carriers and porous inorganic carriers, and the porous inorganic carrier is preferable. The average pore diameter of the porous carrier is preferably 1 nm to 100 µm, and more preferably 5 nm to 5 µm. Suitable porous organic carriers are polymeric substances composed of, for example, polystyrene, polyacrylamide and polyacrylate; and suitable porous inorganic carriers are, for example, silica, alumina, zirconia, magnesia, glass, kaolin, titanium oxide, silicate salts and hydroxyapatite. The forms of the above porous inorganic carriers may be not only particulate carriers, but also network inorganic carriers like organic mineral composites, and cylindrical monolithic inorganic carriers held in columns, described in Japanese Patent Application Laid-Open Nos. 2005-17268 and 2006-150214.

A particularly preferable carrier is silica gel, and the average particle diameter of the silica gel is preferably 1 µm to 1 mm, more preferably 1 µm to 300 µm, and still more preferably 1 µm to 100 µm. The carrier may be subjected to a pre-treatment for improving the affinity of the carrier for the polysaccharide derivative or for improving the surface characteristics of the carrier itself. A method of treating the surface of the carrier is, for example, silane finishing with an organic silane compound or a surface treatment method by plasma polymerization. The amount of the polysaccharide derivative carried on a carrier is preferably 1 to 100 parts by mass, more preferably 5 to 60 parts by mass, and particularly preferably 10 to 40 parts by mass, based on 100 parts by mass of the separating agent for optical isomers.

The polysaccharide derivative according to the present embodiment can be used also for the separation of, for example, diastereomers, in addition to the usage as a separating agent for optical isomers.

EXAMPLES

Hereinafter, the present invention will be described in more detail by way of Examples, but the present invention is not limited to these Examples.

Example 1

First, cellulose tris(3,5-dichlorophenylcarbamate) was synthesized according to the method described in Y. Okamoto, M. Kawashima and K. Hatada, J. Chromatogr., 363, 173 (1986). A $^1$H-NMR spectrum chart (500 MHz) thereof is shown in FIG. 1.

Then, 1.2 g (1.65 mmol) of the obtained cellulose tris(3,5-dichlorophenylcarbamate) was dried at 80° C. for 5 hours in a depressurized two-necked flask in an oil bath. Then, 36 mL of dried DMAc was added into the flask over 12 hours; 2.4 g of LiCl was further added into and stirred in the flask at room temperature for 2 hours; and finally, 16.8 mL of dried pyridine was added into and stirred in the flask at 80° C. for 4 hours. A solution was thus obtained in which the cellulose tris(3,5-dichlorophenylcarbamate) was homogeneously dissolved in a mixed solvent of DMAc/LiCl/pyridine.

Then, 9.6 mL (68.23 mmol) of 3,5-dimethylphenyl isocyanate was added to the solution, and caused to react at 80° C. for 48 hours under light shielding by an aluminum foil and a dried nitrogen atmosphere. The reaction scheme thereof is shown below. During the reaction, in order to check a reaction product at each reaction time described later, a part of the solution was taken and added to methanol to thereby cause a precipitate of a cellulose derivative to be produced. For the cellulose derivative further having been subjected to filtration, methanol washing and drying, the content of a 3,5-dimethylphenylcarbamoyl group (DMPC), and the ratios of a 3,5-dimethylphenylcarbamoyl group (DMPC) and a 3,5-dichlorophenylcarbamoyl group (DCPC) at the 2-position, 3-position and 6-position in the structural unit of the cellulose derivative were analyzed by $^1$H-NMR and calculated. The results are shown in Table 1. $^1$H-NMR spectrum charts (500 MHz) of the reaction products during the reaction (20 min, 1 hour, 2 hours, 3 hours, 5 hours, 7 hours, 9 hours, 11 hours and 13 hours after the start of the reaction) are shown in FIGS. 2 to 9, respectively.

[Formula 1]

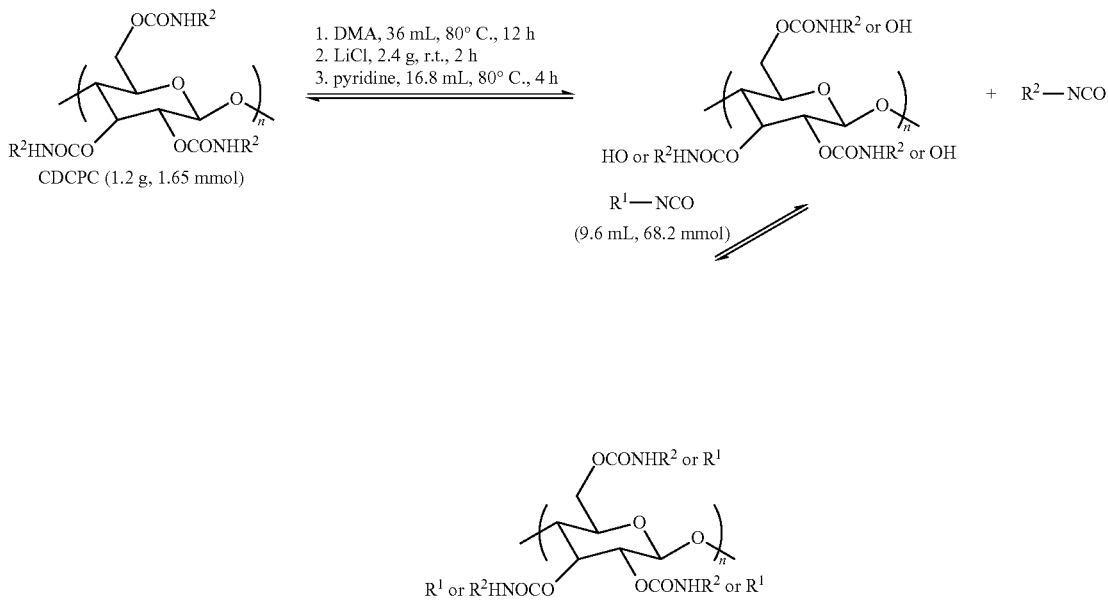

CDCPC (1.2 g, 1.65 mmol)

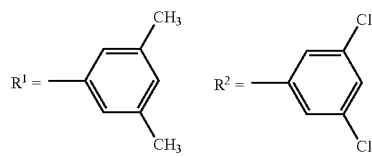

TABLE 1

| | Content of DCPC (mol %) | DCPC:DMPC of 2-Position (molar ratio) | DCPC:DMPC of 3-Position (molar ratio) | DCPC:DMPC of 6-Position (molar ratio) |
|---|---|---|---|---|
| Before Reaction | 100 | 100:0 | 100:0 | 100:0 |
| 20 min | 97.1 | 100:0 | 100:0 | 91:9 |
| 1 hour | 84.8 | 100:0 | 92:8 | 62:38 |
| 2 hours | 56.8 | 98:2 | 68:32 | 19:81 |
| 3 hours | 37.9 | 77:23 | 38:62 | 0:100 |
| 5 hours | 27.3 | 56:44 | 20:80 | 0:100 |
| 7 hours | 19.0 | 45:55 | 14:86 | 0:100 |
| 9 hours | 17.9 | 33:67 | 14:86 | 0:100 |
| 11 hours | 7.1 | 25:75 | 2:98 | 0:100 |
| 13 hours | 3.8 | 14:86 | 0:100 | 0:100 |
| 24 hours | 0 | 0:100 | 0:100 | 0:100 |
| 48 hours | 0 | 0:100 | 0:100 | 0:100 |

Example 2

Figure 10:
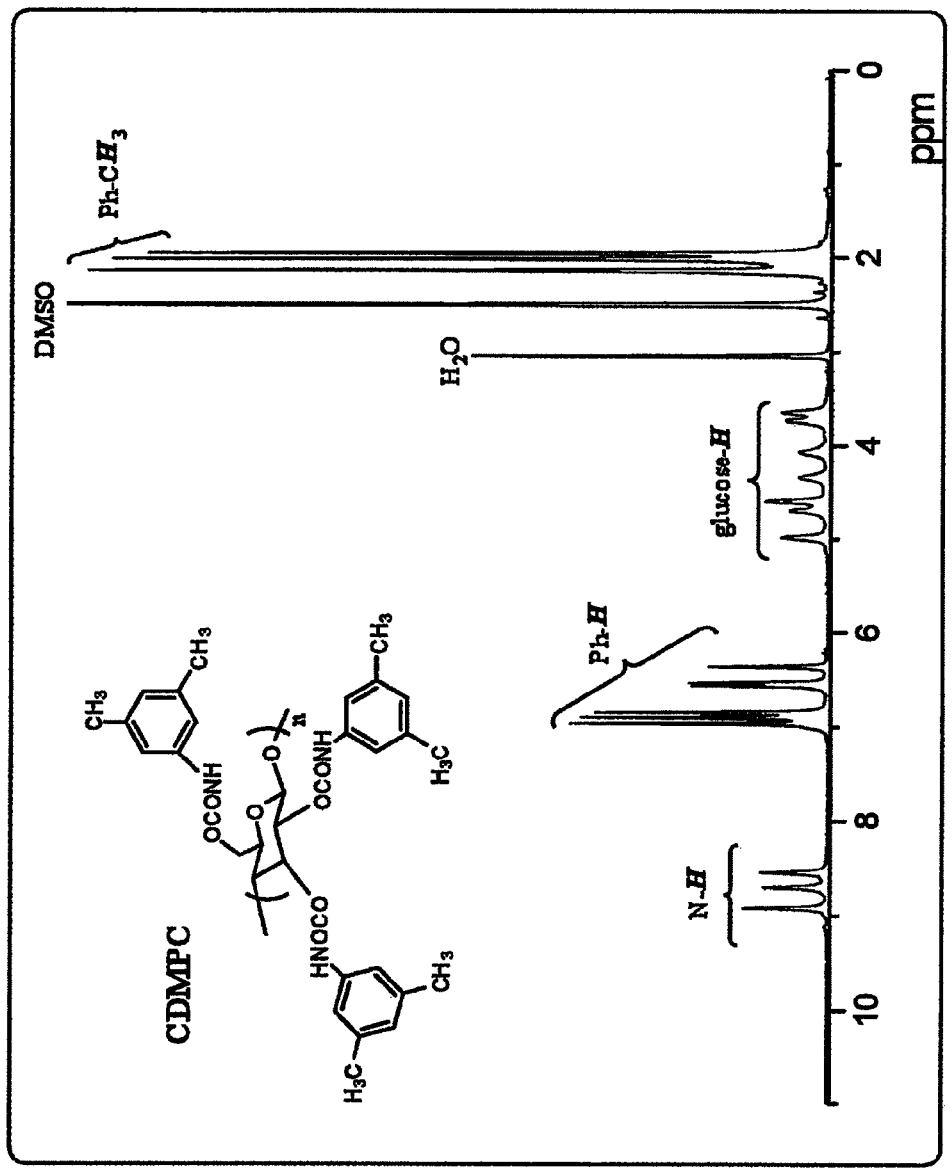
FIG. 10 is a view showing a $^1$H-NMR spectrum of cellulose tris(3,5-dimethylphenylcarbamate).
Figure 11:
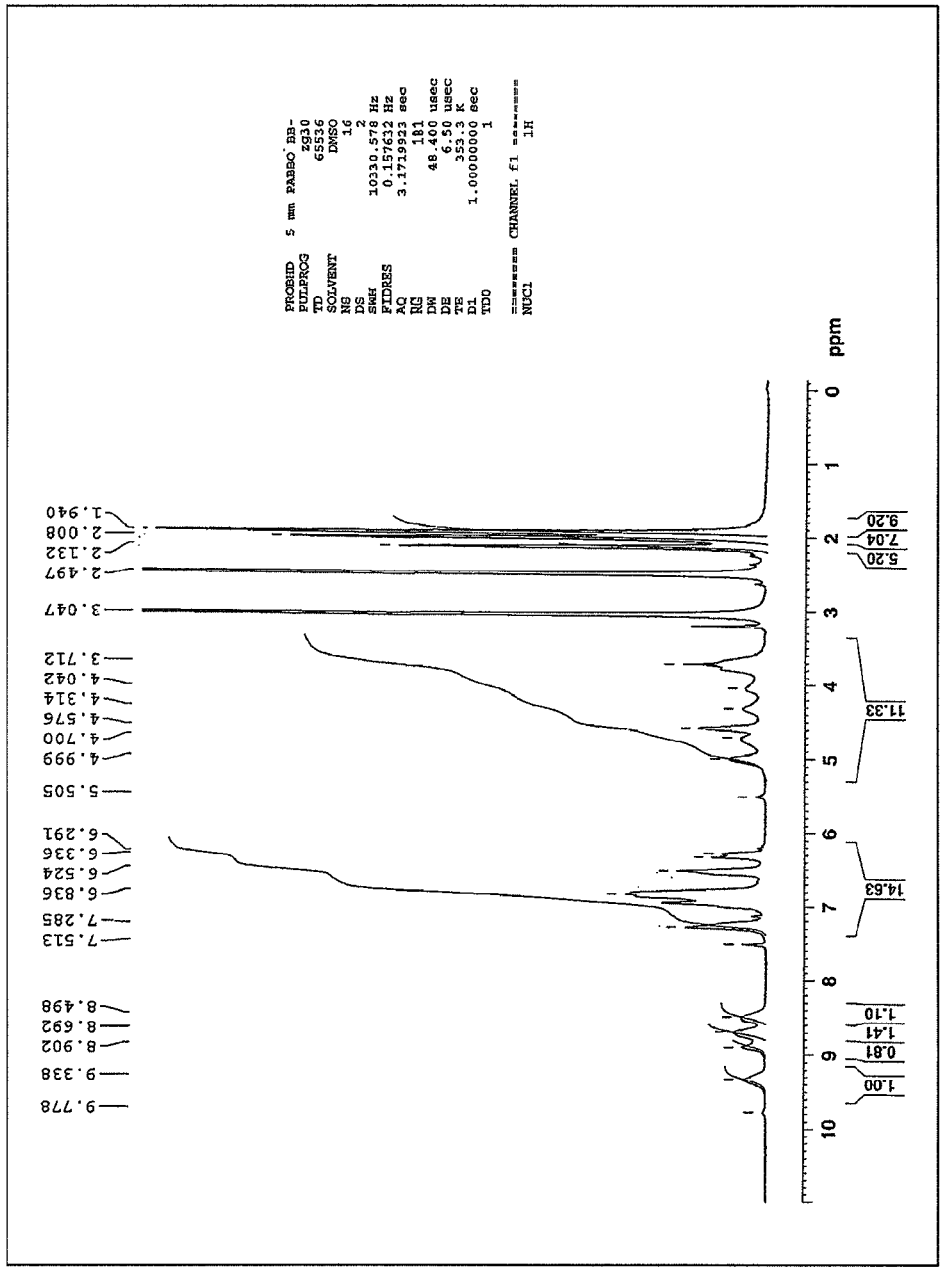
FIG. 11 is a view showing a $^1$H-NMR spectrum of a reaction product when the polysaccharide derivative according to the present invention is produced.
Figure 12:
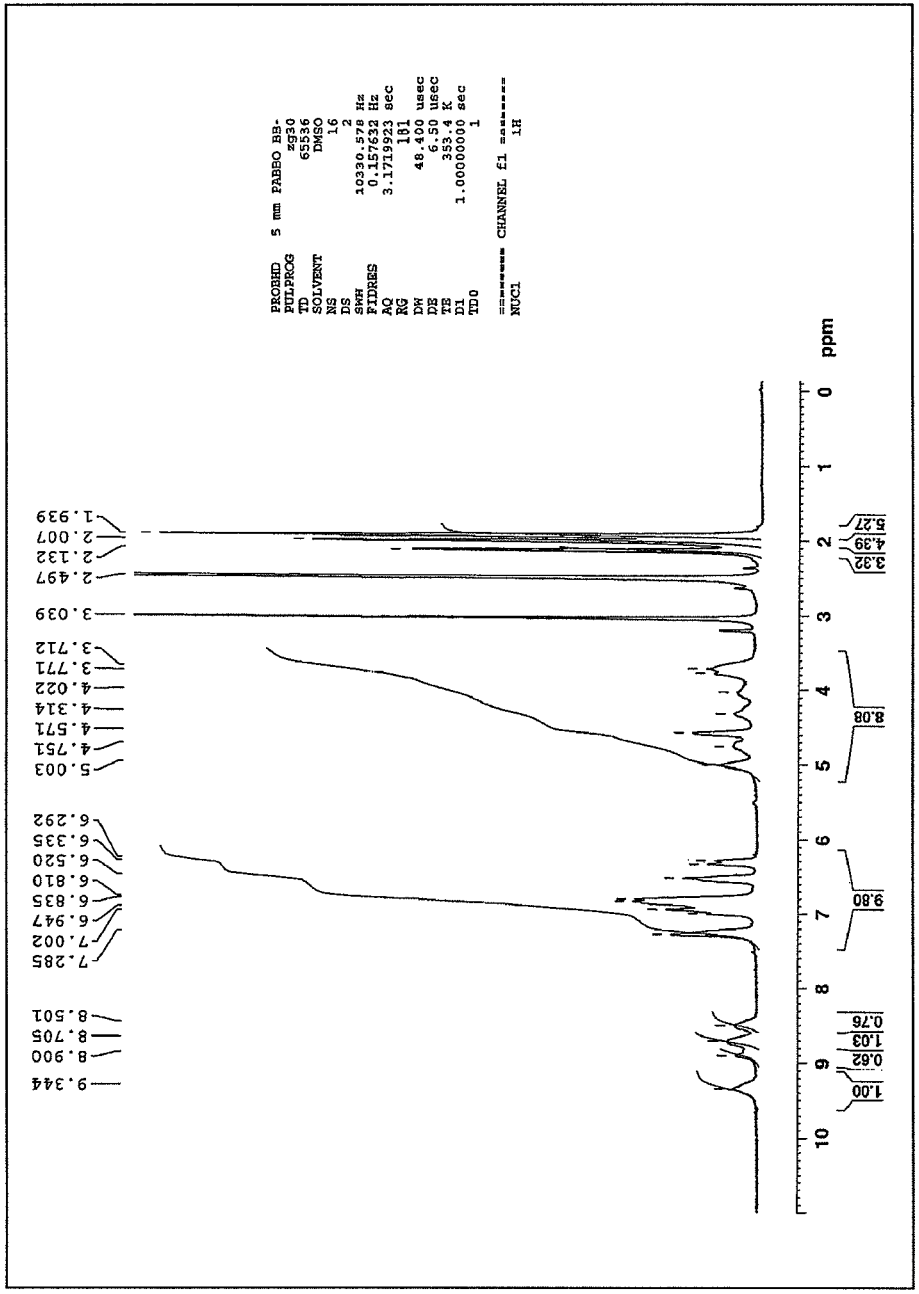
FIG. 12 is a view showing a $^1$H-NMR spectrum of a reaction product when the polysaccharide derivative according to the present invention is produced.
Figure 13:
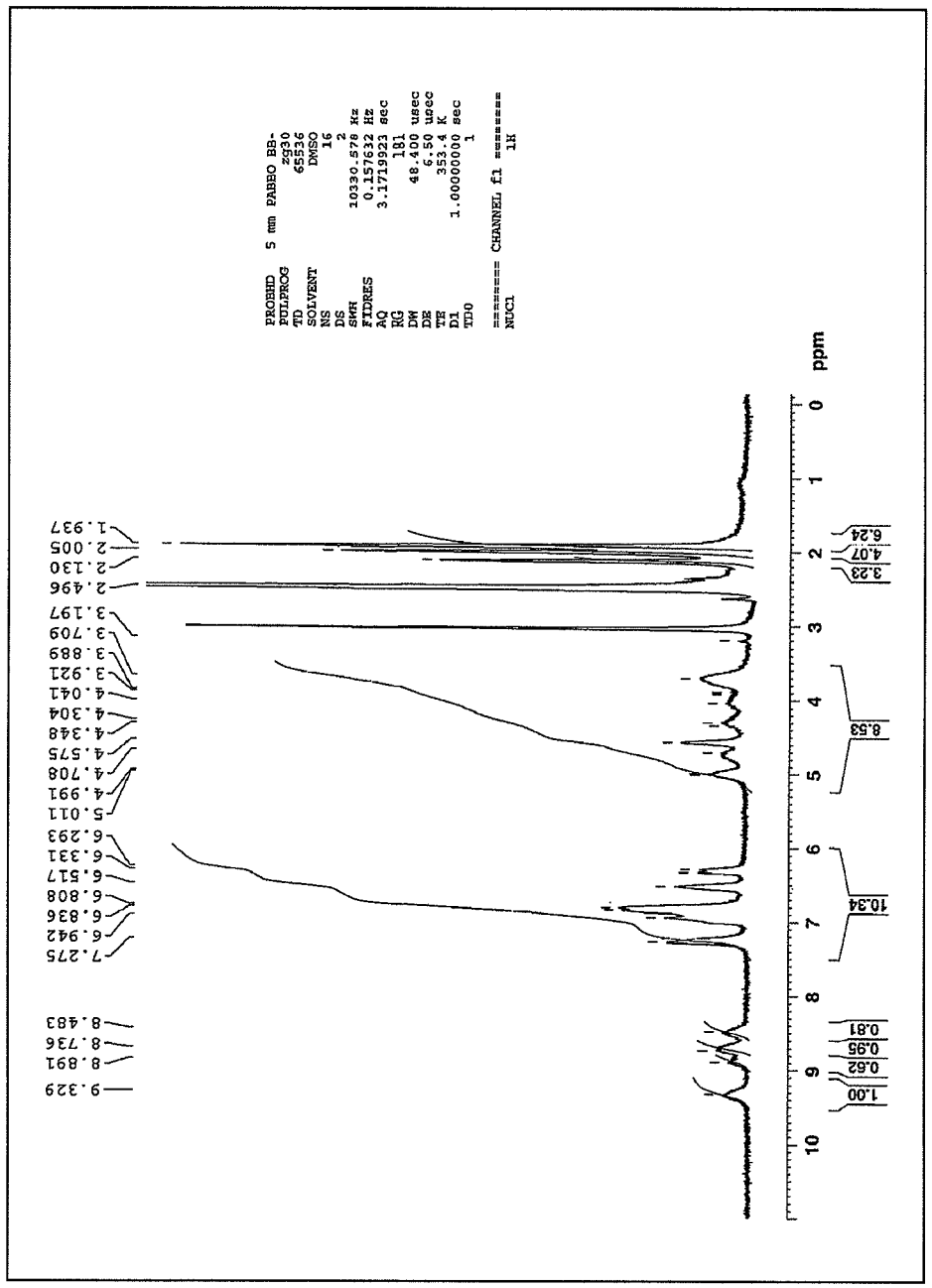
FIG. 13 is a view showing a $^1$H-NMR spectrum of a reaction product when the polysaccharide derivative according to the present invention is produced.
Figure 14:
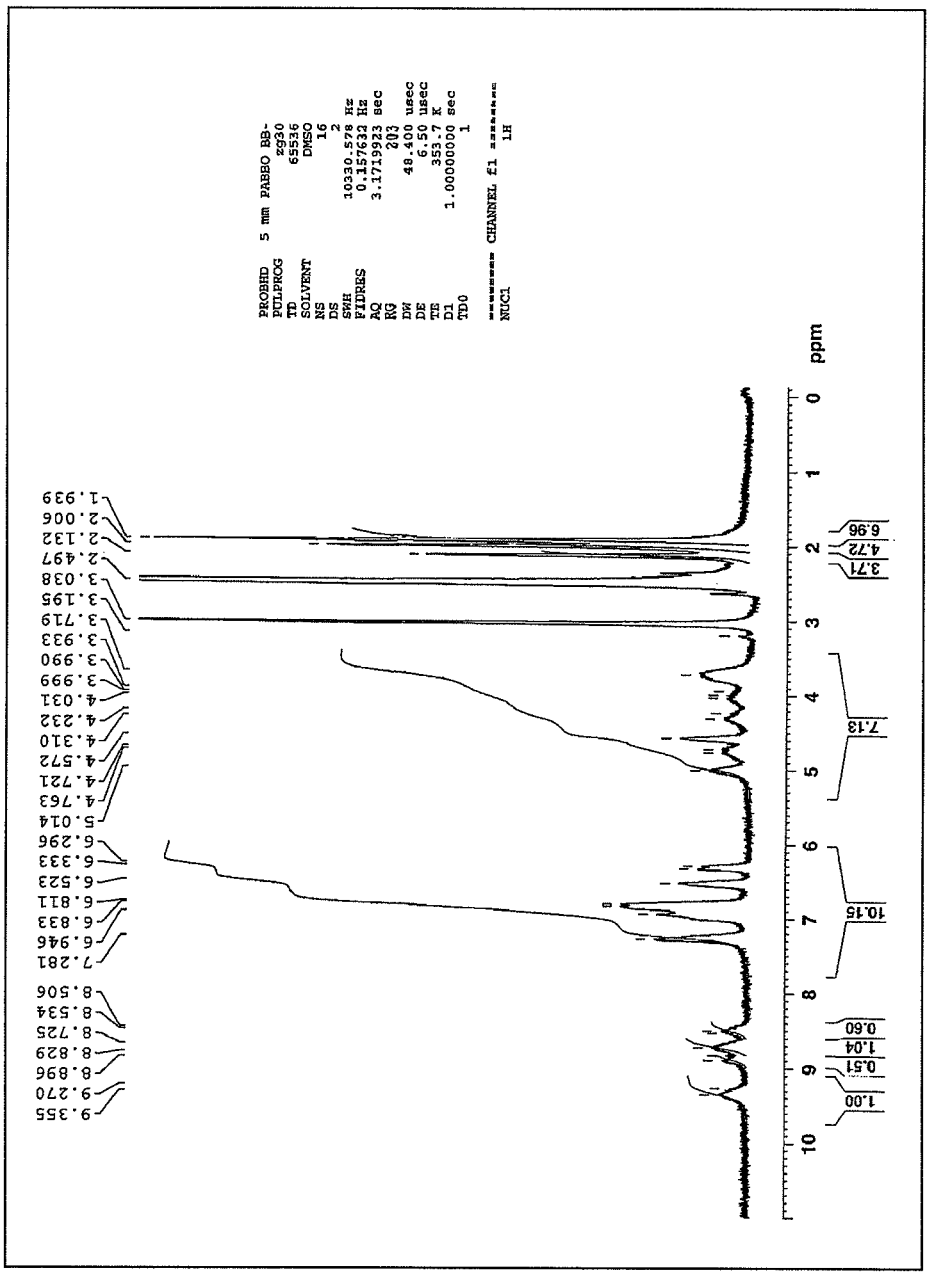
FIG. 14 is a view showing a $^1$H-NMR spectrum of a reaction product when the polysaccharide derivative according to the present invention is produced.
Figure 15:
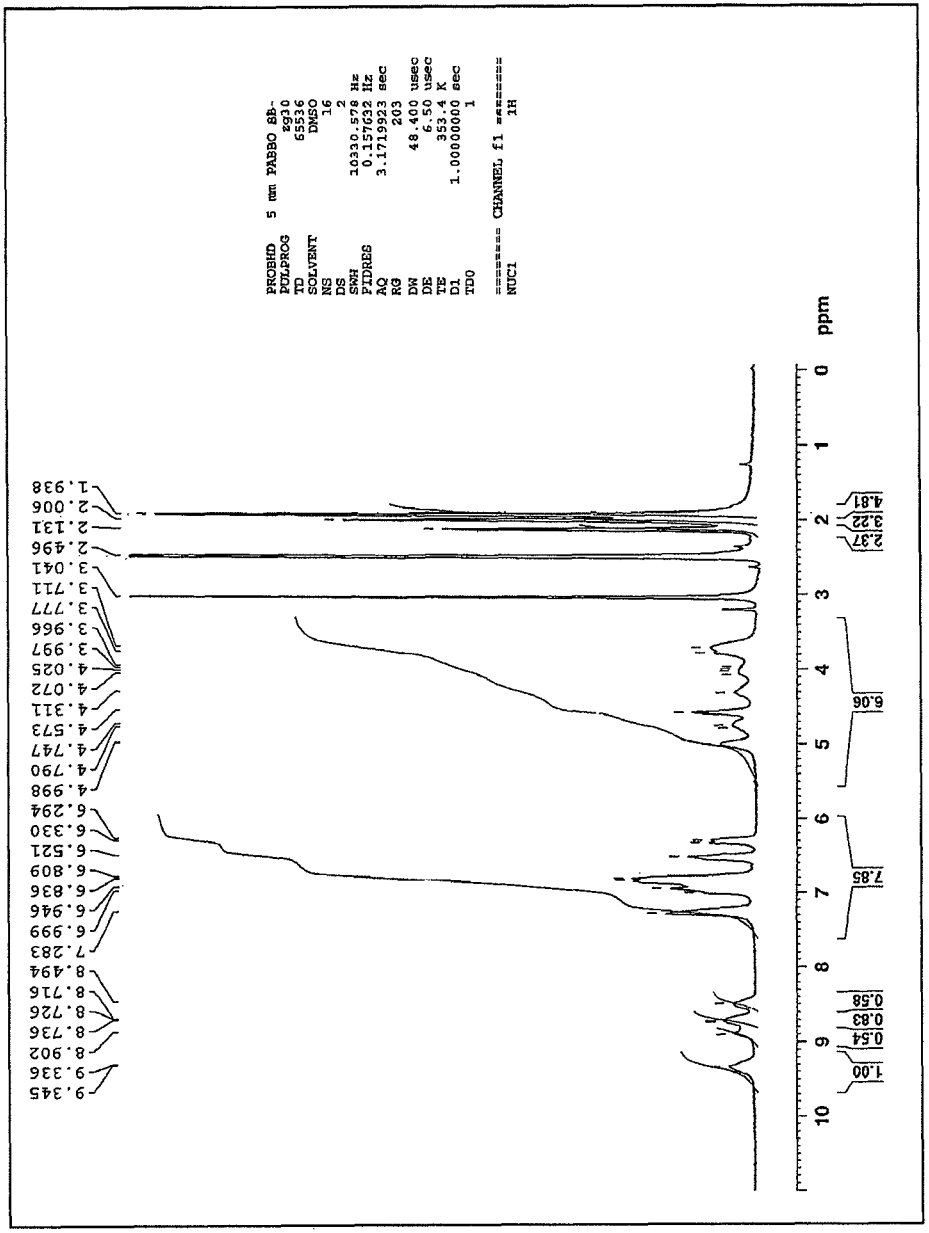
FIG. 15 is a view showing a $^1$H-NMR spectrum of a reaction product when the polysaccharide derivative according to the present invention is produced.
Figure 16:
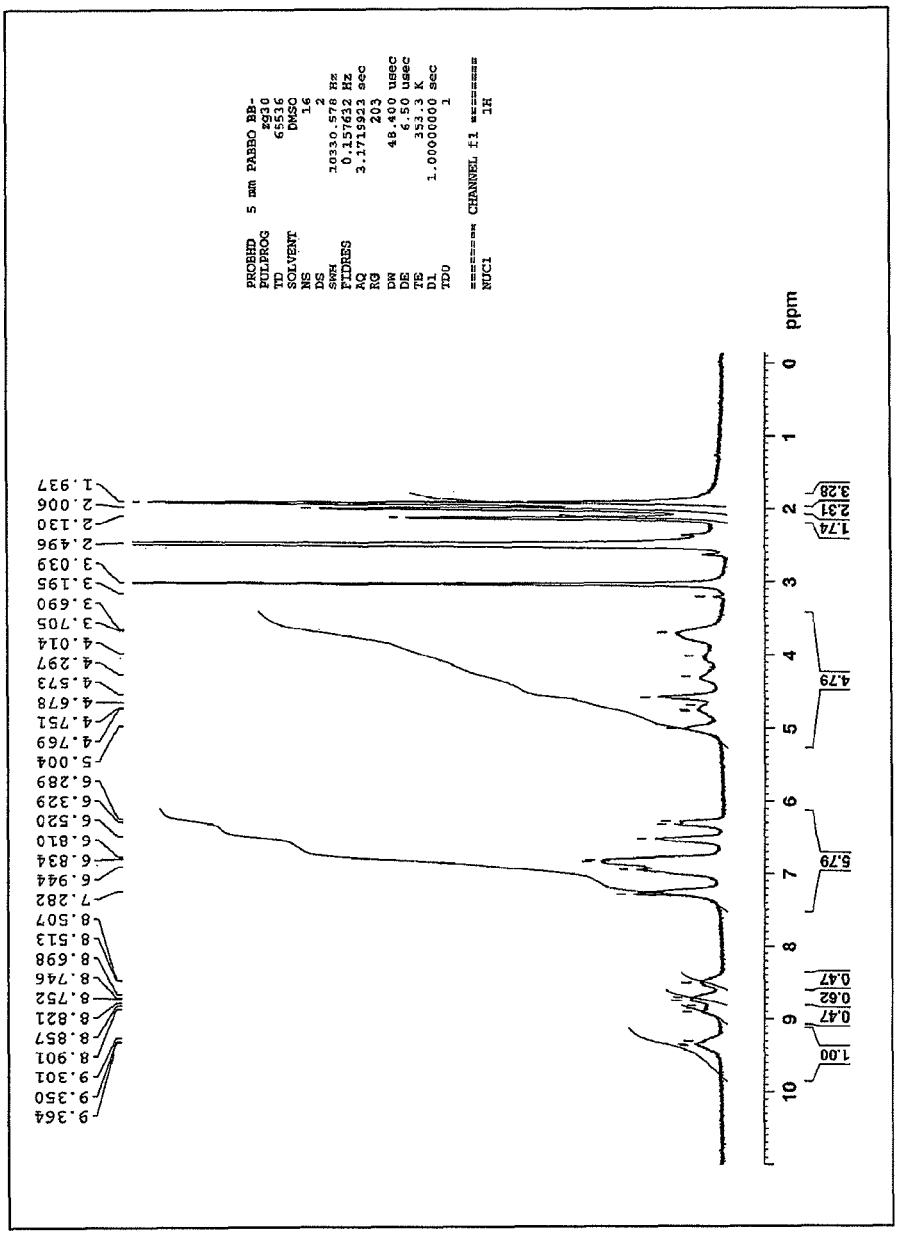
FIG. 16 is a view showing a $^1$H-NMR spectrum of a reaction product when the polysaccharide derivative according to the present invention is produced.
Figure 17:
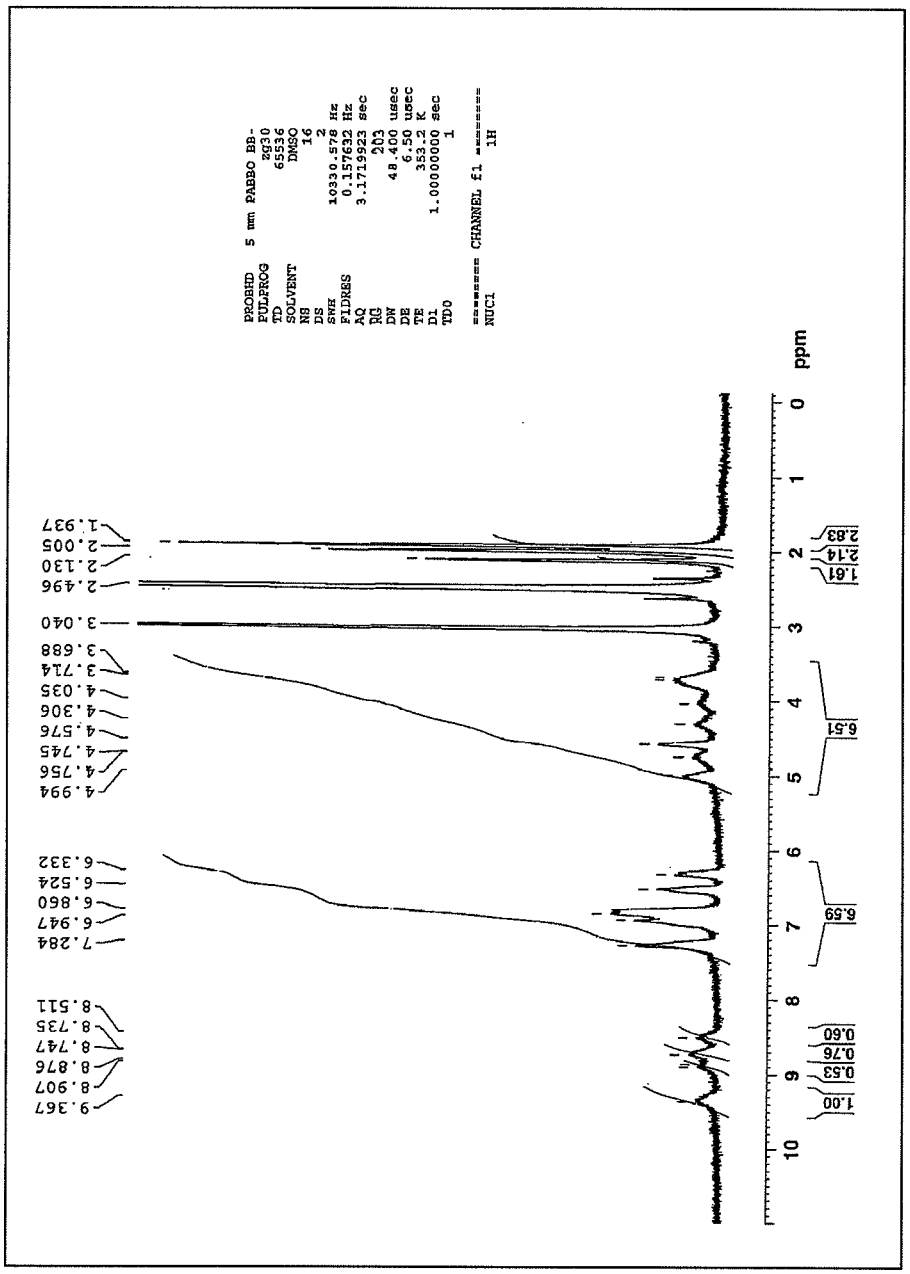
FIG. 17 is a view showing a $^1$H-NMR spectrum of a reaction product when the polysaccharide derivative according to the present invention is produced.
Figure 18:
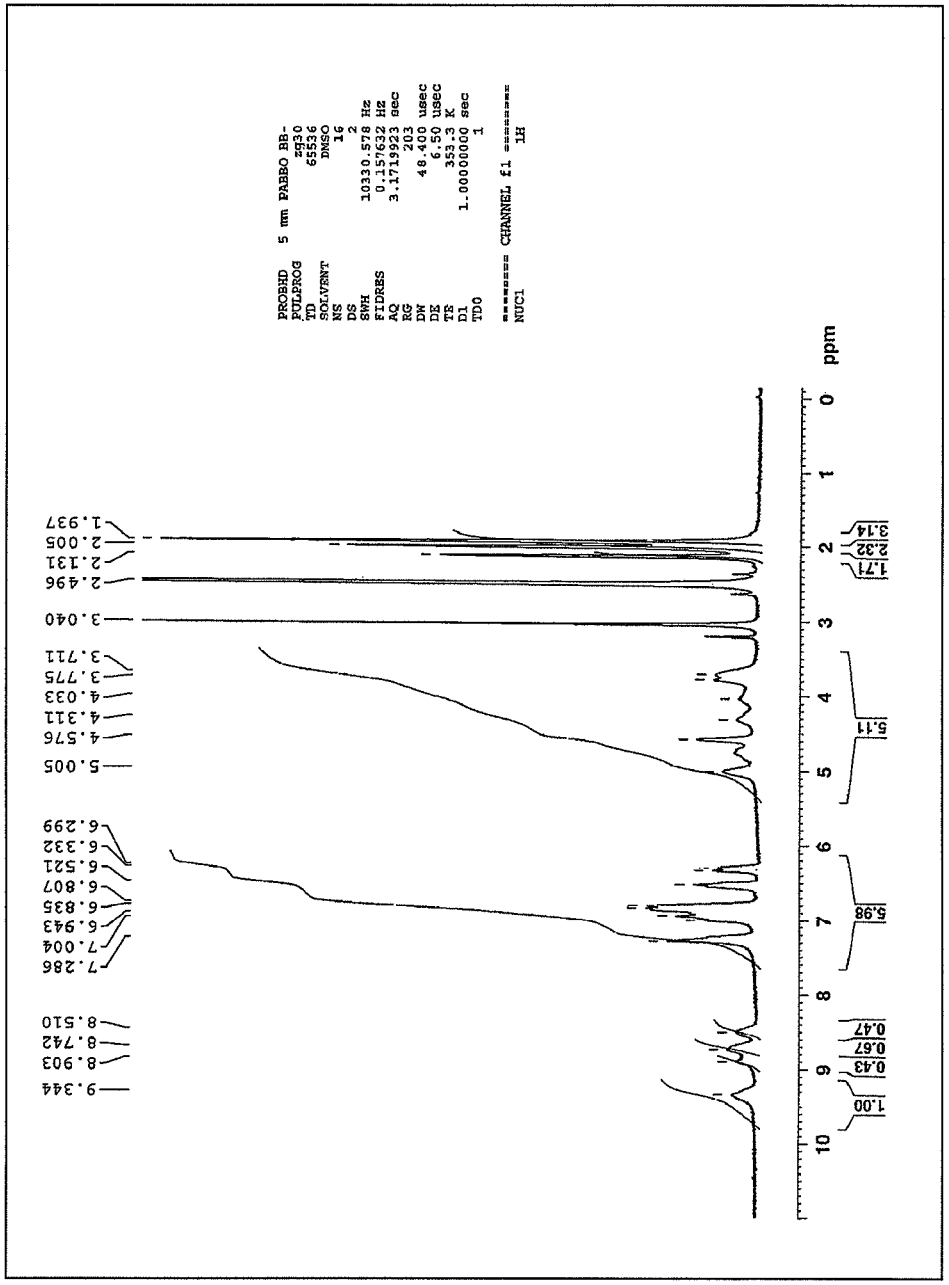
FIG. 18 is a view showing a $^1$H-NMR spectrum of a reaction product when the polysaccharide derivative according to the present invention is produced.

First, cellulose tris(3,5-dimethylphenylcarbamate) was synthesized according to the method described in Y. Okamoto, M. Kawashima and K. Hatada, J. Chromatogr., 363, 173 (1986). A $^1$H-NMR spectrum chart (500 MHz) thereof is shown in FIG. 10.

Then, 1.2 g (1.99 mmol) of the obtained cellulose tris(3,5-dimethylphenylcarbamate) was dried at 80° C. for 5 hours in a depressurized two-necked flask in an oil bath. Then, 36 mL of dried DMAc was added into the flask over 12 hours; 2.4 g of LiCl was further added into and stirred in the flask at room temperature for 2 hours; and finally, 16.8 mL of dried pyridine was added into and stirred in the flask at 80° C. for 4 hours. A solution was thus obtained in which the cellulose tris(3,5-dimethylphenylcarbamate) was homogeneously dissolved in a mixed solvent of DMAc/LiCl/pyridine.

Then, 5.6 g (26.60 mmol) of 3,5-dimethylphenyl isocyanate was added to the solution, and caused to react at 80° C. for 48 hours under light shielding by an aluminum foil and a dried nitrogen atmosphere. The reaction scheme thereof is shown below. During the reaction, in order to check a reaction product at each reaction time described later, a part of the solution was taken and added to methanol to thereby cause a precipitate of a cellulose derivative to be produced. For the cellulose derivative further having been subjected to filtration, methanol washing and drying, the content of a 3,5-dimethylphenylcarbamoyl group (DMPC), and the ratios of a 3,5-dimethylphenylcarbamoyl group (DMPC) and a 3,5-dichlorophenylcarbamoyl group (DCPC) at the 2-position, 3-position and 6-position in the structural unit of the cellulose derivative were analyzed by $^1$H-NMR and calculated. The results are shown in Table 2. $^1$H-NMR spectrum charts (500 MHz) of the reaction products during the reaction (30 min, 1 hour, 2 hours, 3 hours, 5 hours, 7 hours, 9 hours, 11 hours and 13 hours after the start of the reaction) are shown in FIGS. 11 to 18, respectively.

[Formula 2]

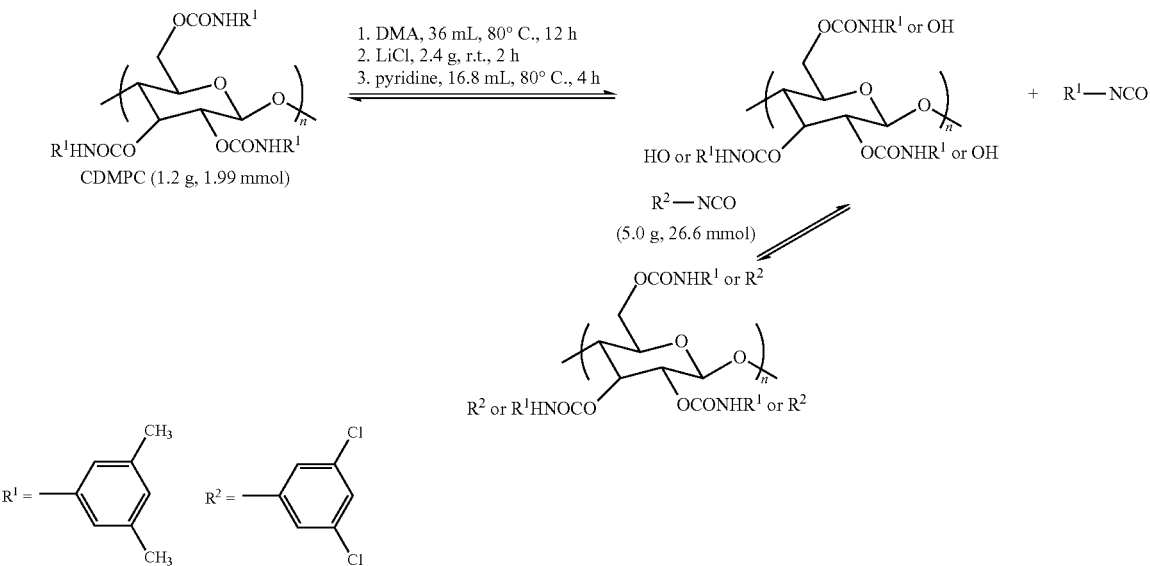

TABLE 2

| | Content of DCPC (mol %) | DCPC:DMPC of 2-Position (molar ratio) | DCPC:DMPC of 3-Position (molar ratio) | DCPC:DMPC of 6-Position (molar ratio) |
|---|---|---|---|---|
| Before Reaction | 0 | 0:100 | 0:100 | 0:100 |
| 30 min | 18.9 | 17:83 | 0:100 | 37:63 |
| 1 hour | 23.0 | 23:77 | 1:99 | 43:57 |
| 2 hours | 28.6 | 32:68 | 8:92 | 44:56 |
| 3 hours | 28.1 | 44:56 | 7:93 | 43:57 |
| 5 hours | 33.0 | 43:57 | 5:95 | 43:57 |
| 7 hours | 33.1 | 40:60 | 14:86 | 44:56 |
| 9 hours | 30.5 | 41:59 | 8:92 | 47:53 |
| 11 hours | 31.1 | 34:66 | 16:84 | 41:59 |
| 13 hours | 35.8 | 42:58 | 17:83 | 47:53 |

Example 3

Figure 19:
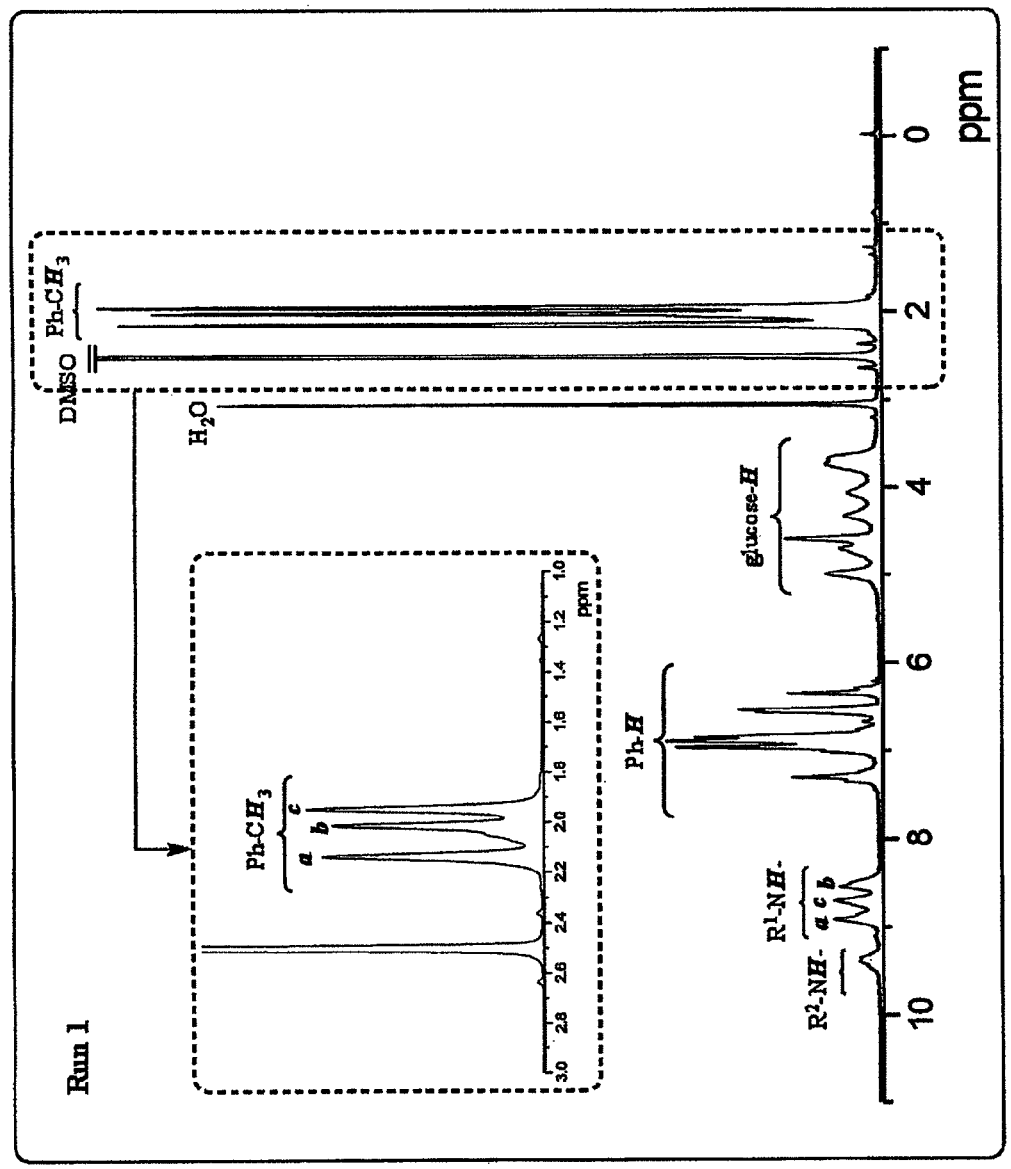
FIG. 19 is a view showing a $^1$H-NMR spectrum of a reaction product when the polysaccharide derivative according to the present invention is produced.

First, 2.5 g of cellulose was dissolved in a mixed solvent of DMAc/LiCl/pyridine (mixing ratio: 7.5 mL/0.5 g/3.75 mL). Then, 0.53 g of 3,5-dichlorophenyl isocyanate was added thereto, and caused to react at 80° C. for 12 hours under a dried nitrogen atmosphere. Then, 2 mL (14.2 mmol) of 3,5-dimethylphenyl isocyanate was added, and successively caused to react at 80° C. for 12 hours under a dried nitrogen atmosphere. The obtained reaction product (cellulose derivative) was caused to precipitate in methanol, and further subjected to filtration, methanol washing and drying to be thereby purified. A $^1$H-NMR spectrum chart (500 MHz) of the reaction product is shown in FIG. 19. The molar ratio of DMPC and DCPC in the reaction product was 83:17. The ratios of DCPC at the 2-position (b), the 3-position (c) and the 6-position (a) were found to be nearly the same.

Example 4

Figure 20:
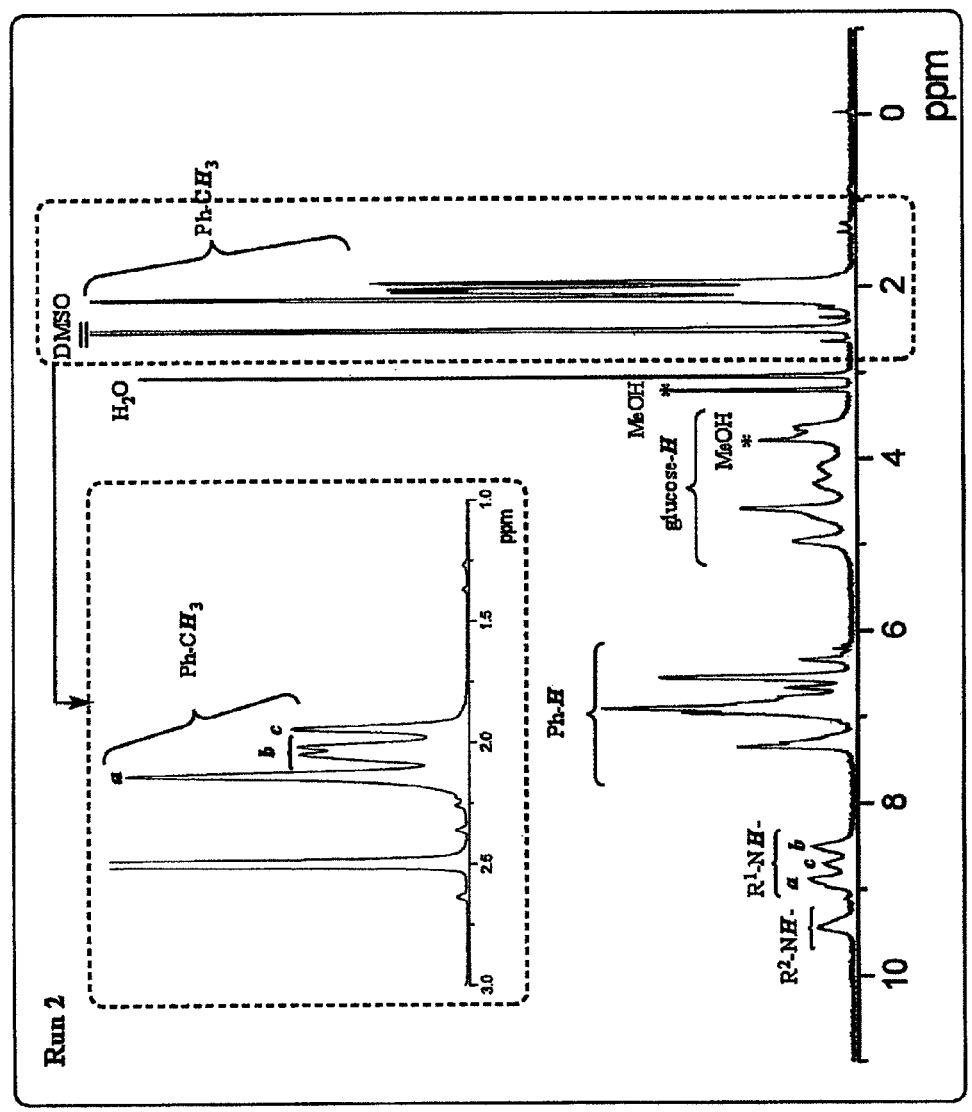
FIG. 20 is a view showing a $^1$H-NMR spectrum of a reaction product when the polysaccharide derivative according to the present invention is produced.

First, 2.5 g of cellulose was dissolved in a mixed solvent of DMAc/LiCl/pyridine (mixing ratio: 7.5 mL/0.5 g/3.75 mL). Then, 1.35 g of 3,5-dichlorophenyl isocyanate was added thereto, and caused to react at 80° C. for 39 hours under a dried nitrogen atmosphere. Then, 2 mL (14.2 mmol) of 3,5-dimethylphenyl isocyanate was added, and successively caused to react at 80° C. for 24 hours under a dried nitrogen atmosphere. The obtained reaction product (cellulose derivative) was caused to precipitate in methanol, and further subjected to filtration, methanol washing and drying to be thereby purified. A $^1$H-NMR spectrum chart (500 MHz) of the reaction product is shown in FIG. 20. The molar ratio of DMPC and DCPC in the reaction product was 73:27. The ratios of DCPC at the 2-position (b), the 3-position (c) and the 6-position (a) were found to be 36:15:49.

Reaction schemes of the above Example 3 (Run 1) and Example 4 (Run 2) are shown below.

Scheme 3. Synthesis of cellulose derivatives by exchange reaction.

[Formula 3]

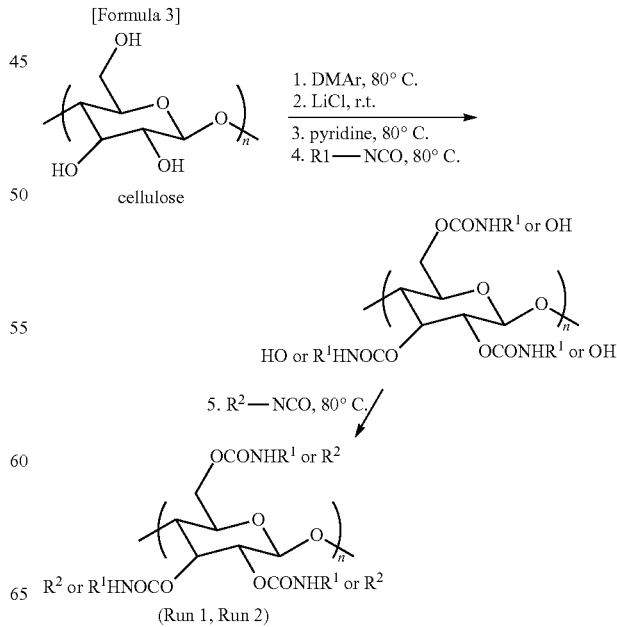

(Run 1, Run 2)

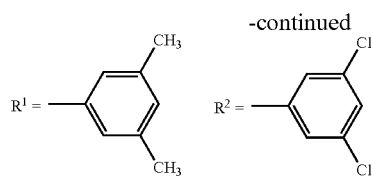

Optical resolving powers of HPLC columns packed with the cellulose derivatives obtained in Examples 3 and 4 were evaluated by optical resolution of racemates 1 to 7 whose structural formulae are shown below. A silica gel (average particle diameter: 7 μm, average pore diameter: 100 nm) was coated with the cellulose derivative of Example 3 or 4 by the method described in Y. Okamoto, M. Kawashima and K. Hatada, J. Chromatogr., 363, 173 (1986), and packed in a column (25 cm in length×0.20 cm in inner diameter) to thereby obtain an HPLC column. The results of TG analysis revealed that the silica gel was coated with 25.0% by mass of the cellulose derivative of Example 3, and with 23.5% by mass of the cellulose derivative of Example 4. The number of plates of the HPLC column was about 2,000.

[Formula 4]

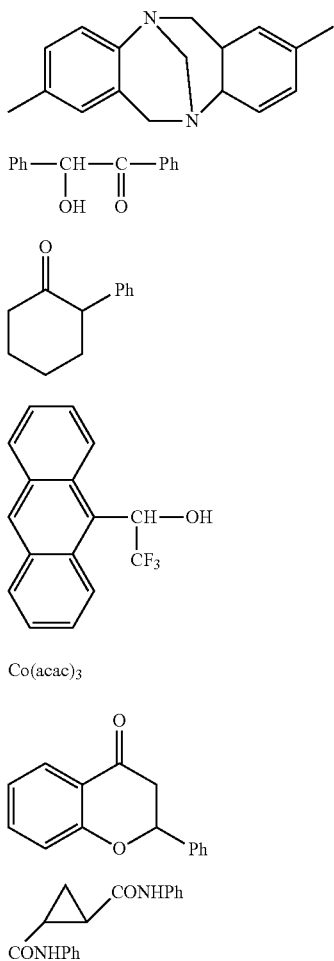

Here, "acac" represents acetylacetonate, and "Ph" represents a phenyl group.

As an eluent, a mixed solvent of n-hexane and 2-propanol (volume ratio=9:1) was used, and the optical resolving power of the HPLC column was examined under the condition of a flow volume of 0.1 mL/min and a column temperature of 20° C. The results are shown in Table 3. The results of the optical resolving powers of cellulose tris(3,5-dimethylphenylcarbamate)(CDMPC) and cellulose tris(3,5-dichlorophenylcarbamate) (CDCPC) described in Y. Okamoto, M. Kawashima and K. Hatada, J. Chromatogr., 363, 173 (1986) as references are together shown in Table 3.

TABLE 3

| | Run 1[a] | | Run 2[a] | | CDMPC[b] | | CDCPC[b] | |
|---|---|---|---|---|---|---|---|---|
| | $R^2$—NHOCO—, % | | | | | | | |
| Race- | 17.3% | | 26.8% | | 0% | | 100% | |
| mates | $k_1'$ | α | $k_1'$ | α | $k_1'$ | α | $k_1'$ | α |
| 1 | 0.90 (+) | 1.18 | 0.52 (+) | 1.42 | 0.97 (+) | 1.32 | 0.87 (+) | 1.65 |
| 2 | 2.21 (+) | 1.60 | 1.51 (+) | 1.29 | 2.43 (+) | 1.58 | 3.08 (−) | 1.21 |
| 3 | 1.02 (−) | 1.14 | 0.95 (−) | ~1 | 1.17 (−) | 1.15 | 2.65 (−) | 1.26 |
| 4 | 1.67 (−) | 2.25 | 0.70 (−) | 1.99 | 2.13 (−) | 2.59 | 0.28 (−) | 1.38 |
| 5 | 0.31 (−) | 1.23 | 0.34 (−) | ~1 | 0.42 (+) | ~1 | 0.76 (+) | 1.82 |
| 6 | 1.14 (−) | 1.40 | 0.83 (−) | 1.21 | 1.47 (−) | 1.41 | 1.55 (−) | 1.20 |
| 7 | 0.72 (+) | 1.64 | 0.54 (+) | 1.44 | 0.83 (+) | 3.17 | 0.59 (+) | 1.41 |
| $\Sigma k_1'$ or $\Sigma\alpha$-7 | 7.97 | 3.44 | 5.39 | 2.53 | 9.42 | 4.22 | 9.78 | 2.93 |

From the results, it is found that for racemates other than racemate 1, the HPLC column relevant to Example 3 exhibited a better optical resolving power than the HPLC column relevant to Example 4. It is also found that for racemate 2, the HPLC column relevant to Example 3 exhibited a better optical resolving power than cellulose tris(3,5-dimethylphenylcarbamate) and cellulose tris(3,5-dichlorophenylcarbamate). The polysaccharide derivative according to the present invention was thus found to be able to function as a novel separating agent for optical isomers and exhibit an optical resolving power of great interest.

INDUSTRIAL APPLICABILITY

The polysaccharide derivative according to the present invention has industrial applicability in separating agents including separating agents for optical isomers.

The invention claimed is:

1. A method of producing a product polysaccharide derivative having a structure in which a hydrogen atom of a hydroxyl group or an amino group at the 2-position in a structural unit of a polysaccharide is substituted with a monovalent group represented by the following general formula (1) and a hydrogen atom of a hydroxyl group or an amino group at the 3-position in the structural unit is substituted with a monovalent group represented by the following general formula (2)

$R^1$—NH—CO—     (1)

$R^2$—NH—CO—     (2)

where $R^1$ and $R^2$ represent aryl groups substituted with one or more substituents selected from the group consisting of hydrocarbon groups that have 1 to 12 carbon atoms, which may optionally contain a hetero atom, a cyano group, halogen atoms, a hydroxy group, a nitro group, an amino group, and amino groups having alkyl groups having 1 to 8 carbon atoms as substituents or unsubstituted aryl groups, $R^1$ and $R^2$ being different from each other, comprising the steps of:

preparing a solvent mixture comprising a solvent, a raw material polysaccharide derivative in which hydrogen atoms of hydroxyl groups or amino groups at the 2-position, 3-position and 6-position in a structural unit of the polysaccharide are substituted with monovalent groups identical to each other represented by formula (1), and an ionic compound for promoting the dissolution of the raw material polysaccharide derivative in the solvent; and bringing the solvent mixture into contact with a compound represented by the following general formula (3) to substitute one of the monovalent groups represented by general formula (1) with a monovalent group represented by general formula (2) to form the product polysaccharide derivative, $$R^2-NCO \qquad (3).$$

* * * * *